United States Patent
James et al.

(10) Patent No.: US 8,409,138 B2
(45) Date of Patent: Apr. 2, 2013

(54) DELAY MECHANISM FOR AUTOMATIC INJECTION DEVICE

(75) Inventors: Adrian Benton James, Oakland, CA (US); Robert Ian Lister, Sunnyvale, CA (US); Paul Joseph Silberschatz, San Francisco, CA (US); Brian Joseph Mason, Menlo Park, CA (US)

(73) Assignee: Eli Lilly and Company, Indianapolis, IN (US)

( * ) Notice: Subject to any disclaimer, the term of this patent is extended or adjusted under 35 U.S.C. 154(b) by 141 days.

(21) Appl. No.: 12/529,788

(22) PCT Filed: Mar. 5, 2008

(86) PCT No.: PCT/US2008/055892
§ 371 (c)(1),
(2), (4) Date: Sep. 3, 2009

(87) PCT Pub. No.: WO2008/112472
PCT Pub. Date: Sep. 18, 2008

(65) Prior Publication Data
US 2010/0049125 A1    Feb. 25, 2010

Related U.S. Application Data

(60) Provisional application No. 60/893,996, filed on Mar. 9, 2007.

(51) Int. Cl.
*A61M 5/00* (2006.01)
(52) U.S. Cl. .................... 604/110; 604/210; 606/272
(58) Field of Classification Search .................. 604/107, 604/110, 157, 208, 210, 242; 606/272
See application file for complete search history.

(56) References Cited

U.S. PATENT DOCUMENTS

| 2,752,918 A | 7/1956 | Uytenbogaart |
| 4,561,856 A | 12/1985 | Cochran |

(Continued)

FOREIGN PATENT DOCUMENTS

| EP | 0470977 | 2/1992 |
| EP | 0 653 220 A1 | 5/1995 |

(Continued)

*Primary Examiner* — Nicholas Lucchesi
*Assistant Examiner* — Gerald Landry, II
(74) *Attorney, Agent, or Firm* — Edward J. Prein

(57) ABSTRACT

A delay mechanism for staging the operation of an automatic injection apparatus (20) to ensure medication contents are properly delivered prior to the needled syringe (32) of the apparatus being retracted. In one form, the delay mechanism includes a shuttle (50), a follower (110), a locking member, a damping compound, and a driver and a driver biasing element (44). The shuttle is for a needled syringe of the apparatus and includes a first latching element. The follower includes a second latching element and a cammable surface, which second latching element is for cooperating with the first latching element to limit motion of the shuttle relative to the follower in a second direction opposite the first direction. The locking member is movable from a locking position to a release position by engagement with the syringe plunger during an injection, the locking member, when in the locking position, preventing rotation of the follower relative to the shuttle, the locking member, when in the release position, allowing rotation of the follower relative to the shuttle. The damping compound is between the follower and a supporting surface to dampen rotation of the follower relative to the shuttle. The driver is rotatably fixed relative to the shuttle and includes a camming surface. The shuttle allowing retracting of the syringe needle into the housing of the automatic injection apparatus after injection.

18 Claims, 33 Drawing Sheets

U.S. PATENT DOCUMENTS

| | | | |
|---|---|---|---|
| 4,744,786 A | 5/1988 | Hooven | |
| 5,080,649 A | 1/1992 | Vetter | |
| 5,300,030 A | 4/1994 | Crossman et al. | |
| 5,346,480 A | 9/1994 | Hess et al. | |
| 5,393,301 A | 2/1995 | Goldberg | |
| 5,514,097 A | 5/1996 | Knauer | |
| 5,779,677 A * | 7/1998 | Frezza | 604/134 |
| 6,077,247 A | 6/2000 | Marshall et al. | |
| 6,159,181 A | 12/2000 | Crossman et al. | |
| 6,221,046 B1 | 4/2001 | Burroughs et al. | |
| 6,258,068 B1 | 7/2001 | Kirchhofer et al. | |
| 6,387,078 B1 | 5/2002 | Gillespie, III | |
| 6,454,743 B1 * | 9/2002 | Weber | 604/131 |
| 6,475,194 B2 | 11/2002 | Domici, Jr. et al. | |
| 6,544,234 B1 | 4/2003 | Gabriel | |
| 6,589,210 B1 | 7/2003 | Rolfe | |
| 6,632,198 B2 | 10/2003 | Caizza | |
| 7,066,907 B2 | 6/2006 | Crossman et al. | |
| 7,097,634 B2 | 8/2006 | Gilbert | |
| 7,361,160 B2 | 4/2008 | Hommann et al. | |
| 7,465,289 B2 | 12/2008 | Marshall | |
| 7,563,252 B2 | 7/2009 | Marshall et al. | |
| 7,635,356 B2 | 12/2009 | Stamp | |
| 7,699,816 B2 | 4/2010 | Kirchhofer et al. | |
| 7,758,548 B2 | 7/2010 | Gillespie et al. | |
| 7,901,377 B1 * | 3/2011 | Harrison et al. | 604/156 |
| 2003/0105430 A1 | 6/2003 | Lavi et al. | |
| 2004/0024367 A1 * | 2/2004 | Gilbert | 604/198 |
| 2006/0184132 A1 | 8/2006 | Watson | |
| 2006/0258990 A1 * | 11/2006 | Weber | 604/208 |
| 2007/0021720 A1 | 1/2007 | Guillermo | |
| 2007/0173770 A1 | 7/2007 | Stamp | |
| 2009/0012470 A1 | 1/2009 | Barrow-Williams | |

FOREIGN PATENT DOCUMENTS

| | | |
|---|---|---|
| EP | 0678303 | 10/1995 |
| EP | 0996473 | 5/2000 |
| ES | 2070782 | 6/1995 |
| GB | 728248 | 4/1955 |
| GB | 2388033 | 11/2003 |
| GB | 2396298 | 6/2004 |
| GB | 2396816 | 7/2004 |
| GB | 2397767 | 8/2004 |
| WO | 9903529 | 1/1999 |
| WO | WO 00/24441 A | 5/2000 |
| WO | WO 03/092771 A1 | 11/2003 |
| WO | WO 03/097133 A1 | 11/2003 |
| WO | WO 2004/054645 | 7/2004 |
| WO | 2005115508 | 12/2005 |
| WO | WO 2005/115512 A1 | 12/2005 |
| WO | WO 2005/115514 A1 | 12/2005 |
| WO | WO 2005/115516 A1 | 12/2005 |
| WO | 2006106291 | 10/2006 |
| WO | WO 2006/106295 | 10/2006 |
| WO | WO 2007/002053 | 1/2007 |
| WO | 2007036676 | 4/2007 |
| WO | WO 2007/036676 | 4/2007 |
| WO | 2009092807 | 7/2009 |
| WO | PCTUS2011025988 | 2/2011 |

* cited by examiner

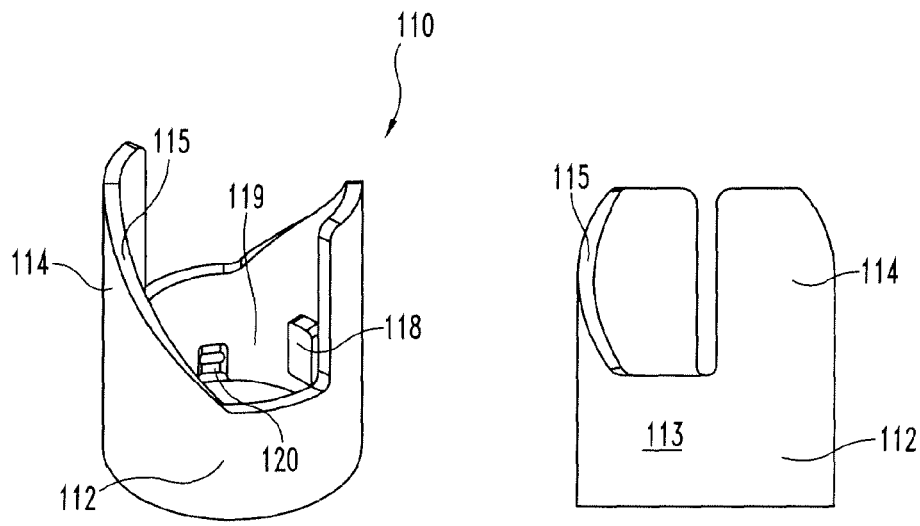
Fig. 9   Fig. 10A
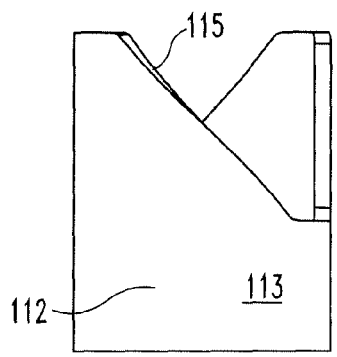   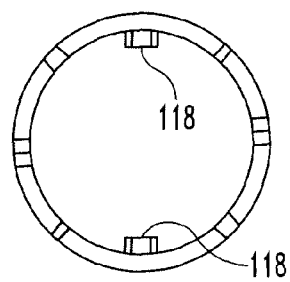
Fig. 10B   Fig. 10C

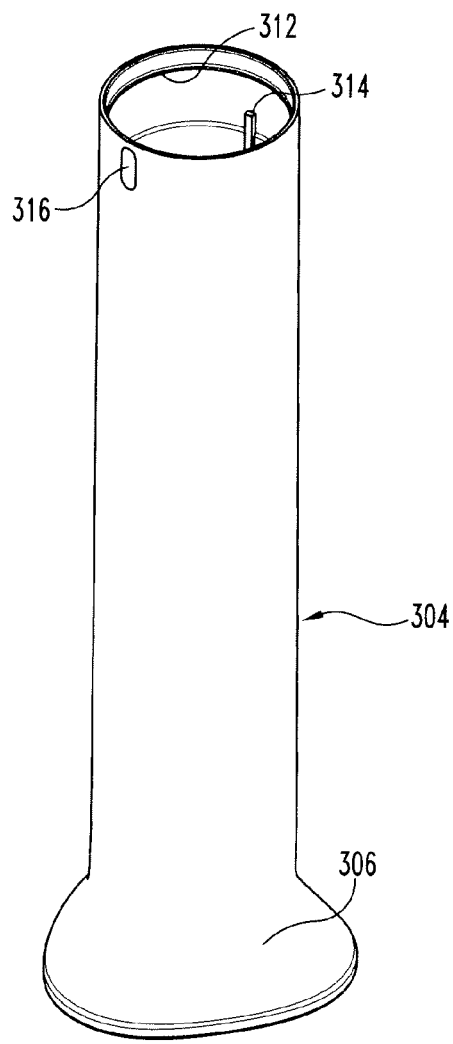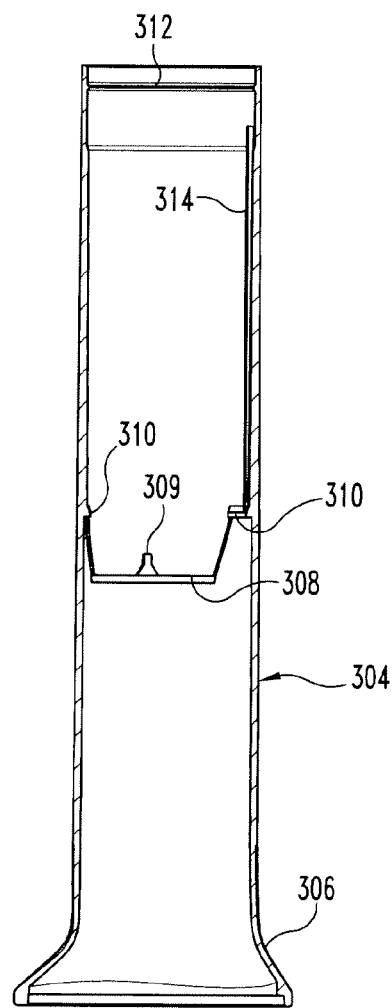
*Fig. 24A*  *Fig. 24B*
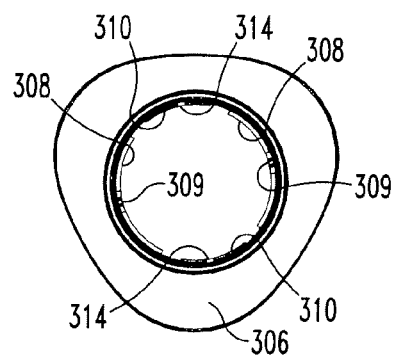
*Fig. 24C*

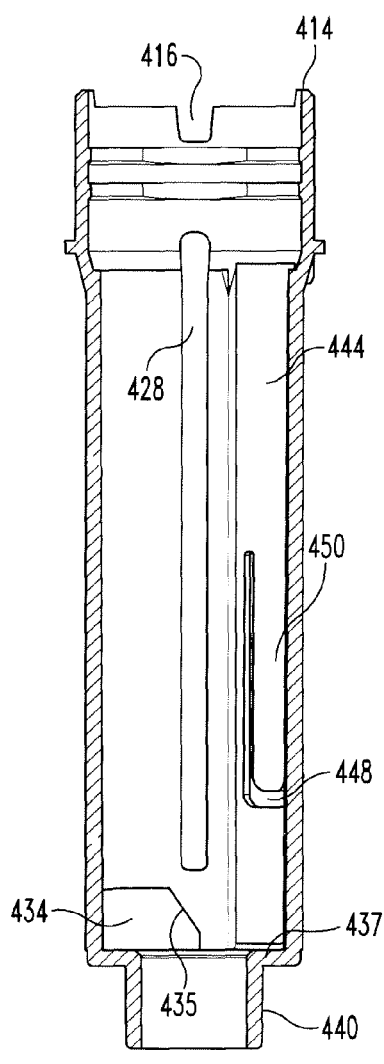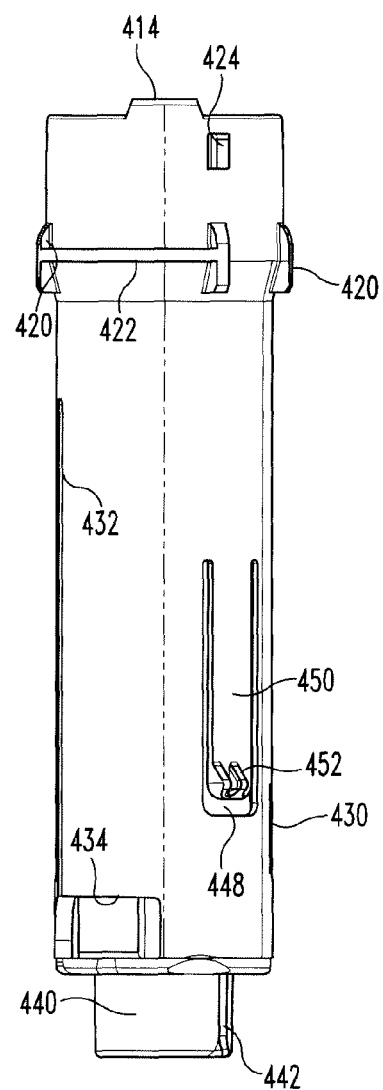
*Fig. 28D*  *Fig. 28C*

DELAY MECHANISM FOR AUTOMATIC INJECTION DEVICE

BACKGROUND OF THE INVENTION

The present invention pertains to pharmaceutical injection devices, and, in particular, to a delay mechanism for an automatic injection device.

Patients suffering from a number of different diseases frequently must inject themselves with pharmaceuticals. A variety of devices have been proposed to facilitate these injections. One type of device is an automatic injection device. This type of device, when triggered by a user, automatically inserts into the user a needle of a syringe that prior to triggering was disposed within the device housing, and then automatically injects a dose of medication through that inserted needle. One known type of automatic injection device then automatically advances a shroud to cover the needle when the dose is completed. In another type of automatic injection device having a configuration more desirable to some, and instead of having an advancing shroud, the device will automatically retract the needle into the housing when the dose is completed. One difficulty with designing an automatic injector with a needle retracting feature is ensuring both that the full desired contents of the syringe have been injected and that the syringe needle is properly retracted into the device housing after use.

International Publication Number WO 2005/115516 explains in additional detail such design difficulty, and further proposes solutions using a type of delay mechanism involving a highly viscous fluid damping. While perhaps functional, these solutions are not without their own shortcomings, such as the delay mechanism being used to transfer force to the syringe during injection.

Thus, it would be desirable to provide a delay mechanism for an automatic injection apparatus that can overcome one or more of these and other shortcomings of the prior art.

BRIEF SUMMARY OF THE INVENTION

In one form thereof, the present invention provides a delay mechanism in an automatic injection apparatus having a housing, a needled syringe with a plunger, and a plurality of biasing elements for moving the needled syringe in a first direction within the housing to extend the needle of the syringe beyond the housing, to advance the plunger to force syringe contents through the needle for an injection, and to retract the needle within the housing after injection. The delay mechanism includes a shuttle for the syringe, the shuttle including a first latching element; a follower including a second latching element and a cammable surface, the second latching element for cooperating with the first latching element to limit motion of the shuttle relative to the follower in a second direction opposite the first direction; a locking member movable within the housing from a locking position to a release position by engagement with the syringe plunger during an injection, the locking member, when in the locking position, preventing rotation of the follower relative to the shuttle, the locking member, when in the release position, allowing rotation of the follower relative to the shuttle; a damping compound between the follower and a supporting surface to dampen rotation of the follower relative to the shuttle; a driver rotatably fixed relative to the shuttle and including a camming surface; and a driver biasing element for forcing the driver from a first position to a second position when the locking member moves to the release position, whereby during movement of the driver to the second position, the driver camming surface engages the follower cammable surface to force the follower to rotate relative to the shuttle from a latching position, at which the first and second latching elements cooperate, to an unlatching position, at which the second latching element is disengaged from the first latching element to allow movement of the shuttle for retracting the syringe needle into the housing after injection.

In another form thereof, the present invention provides a delay mechanism for an automatic injection apparatus, including a shuttle for a needled syringe of the apparatus, a movable member, means for limiting motion of the shuttle in a needle retraction direction, means for damping motion of the movable member relative to the shuttle, and means for moving the movable member relative to the shuttle from a first position to a second position to allow movement of the shuttle for retracting the needle of the syringe within the apparatus after injection.

One advantage of the present invention is that a delay mechanism may be provided which can be adapted for use with differently configured automatic injection devices.

Another advantage of the present invention is that a delay mechanism may be provided for an automatic injection device which is not substantially involved with operational forces applied to the syringe during needle insertion and then injection.

Another advantage of the present invention is that a delay mechanism may be provided for an automatic injection device which allows a timely retraction of the needle without a releasing of the drive actuator from the syringe.

Still another advantage of the present invention is that a delay mechanism may be provided for an automatic injection device which allows a timely retraction of the needle without needing to overcome resistance from the drive actuator of the syringe.

Another advantage of the present invention is that a delay mechanism may be provided for an automatic injection device which uses a damping fluid that need not be displaced from a sealed chamber or forced through a vent.

Still another advantage of the present invention is that a delay mechanism may be provided for an automatic injection device that helps to stage the triggering of the device.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein:

FIG. 9 is a perspective view of the follower of the delay mechanism of FIG. 1, which follower is shown separate from the other components;

FIGS. 10A, 10B, 10C, 10D and 10E are respectively side, front, top, bottom and longitudinal cross-sectional views of the follower of FIG. 9;

FIGS. 24A, 24B and 24C are respectively a perspective, longitudinal cross sectional, and distal end view of the housing body of the apparatus of FIG. 22 shown separate from the other apparatus components;

FIGS. 28A, 28B, 28C, 28D, 28E and 28F are respectively a top perspective, first and second elevational, first and second longitudinal cross-sectional, and distal end views of the lower piece of the shuttle of the apparatus of FIG. 22 shown separate from the other apparatus components;

Figure 1:
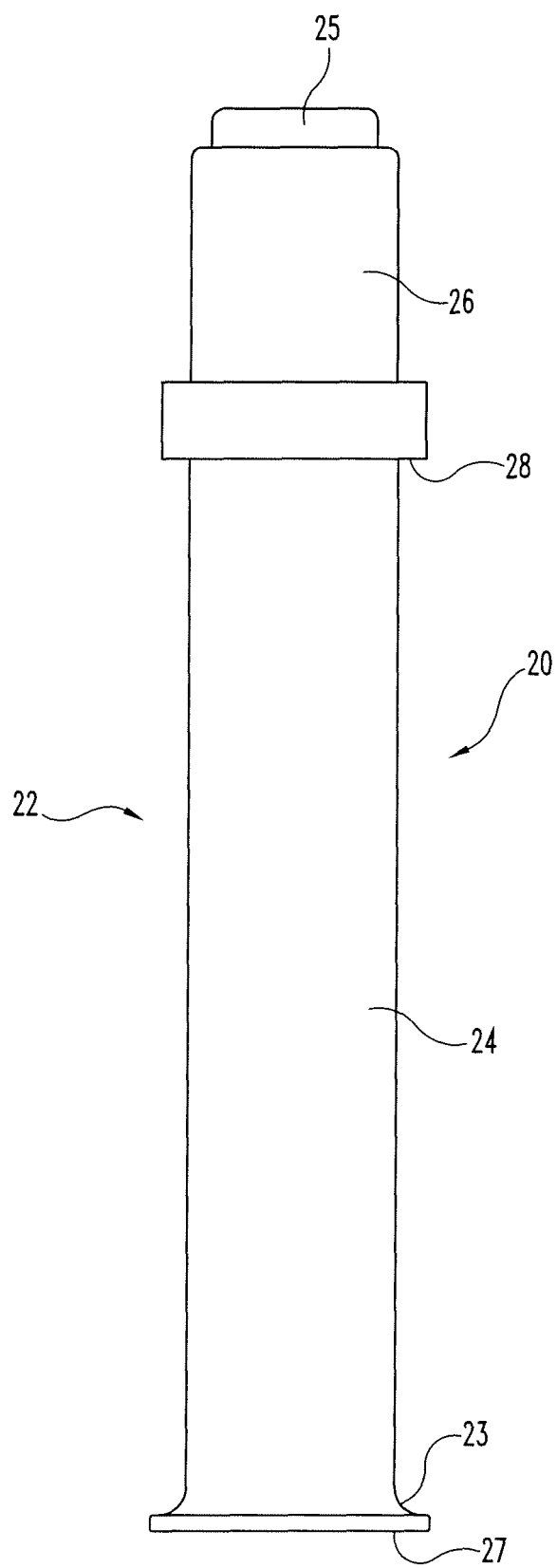
FIG. 1 is a front view of an automatic injection apparatus equipped with a first embodiment of a delay mechanism of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
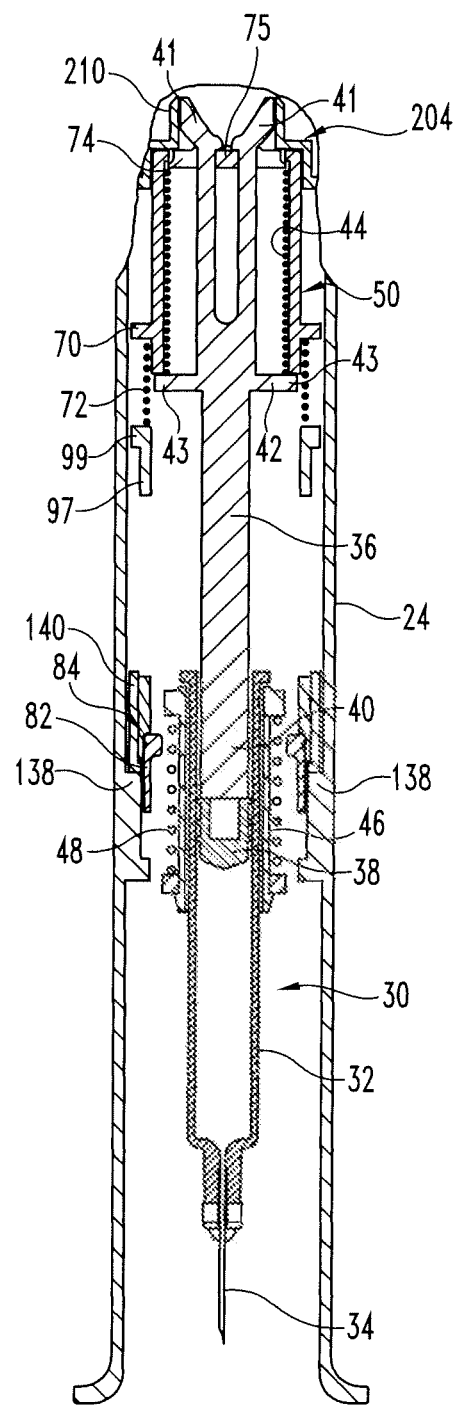
FIG. 2 is a partial front view, in cross section, of the automatic injection apparatus with inventive delay mechanism of FIG. 1.
Figure 3:
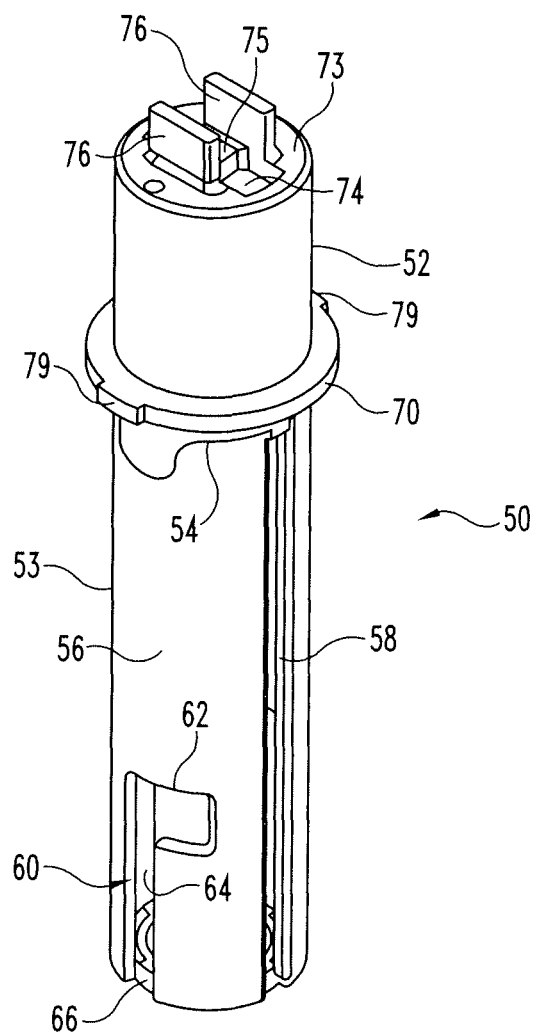
FIG. 3 is a perspective view of the shuttle of the delay mechanism of FIG. 1, which shuttle is shown separate from the other components.
Figure 4A:
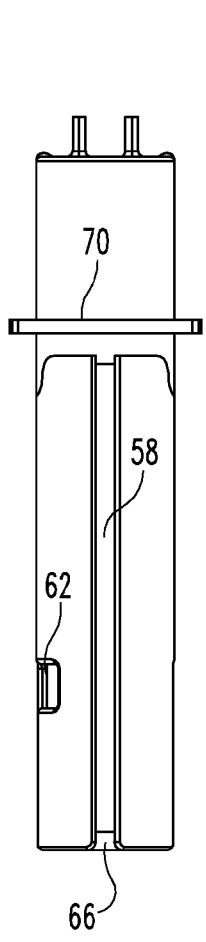
FIGS. 4A, 4B, 4C and 4D are respectively side, front, longitudinal cross-sectional, and top views of the shuttle of FIG. 3.
Figure 4B:
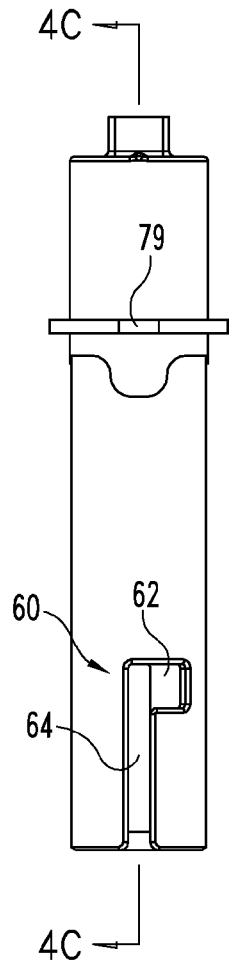
Figure 4C:
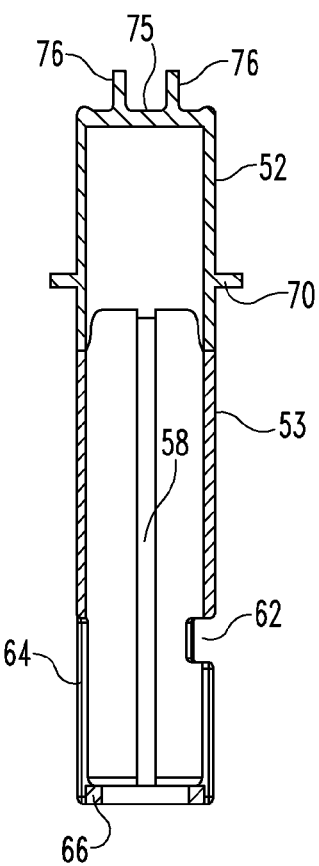
Figure 4D:
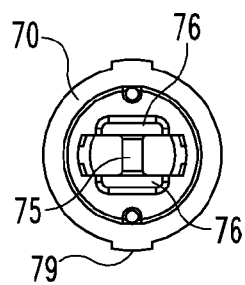
Figure 5:
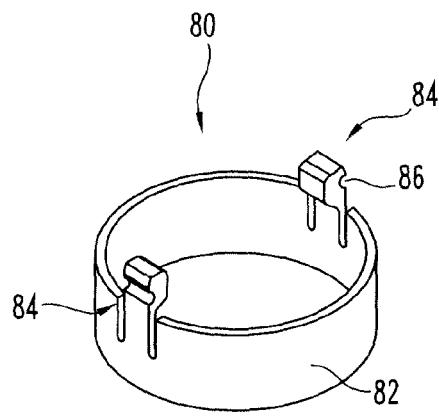
FIG. 5 is a perspective view of the locking member of the delay mechanism of FIG. 1, which locking member is shown separate from the other components.
Figure 6A:
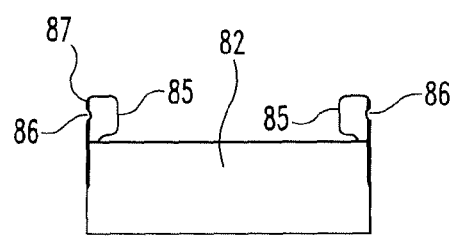
FIGS. 6A, 6B, and 6C are respectively front, side and top views of the locking member of FIG. 5.
Figure 6B:
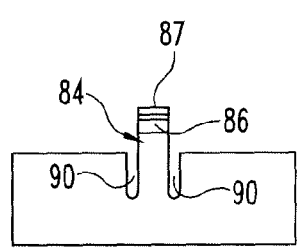
Figure 6C:
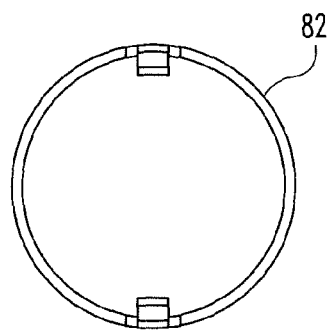
Figure 7:
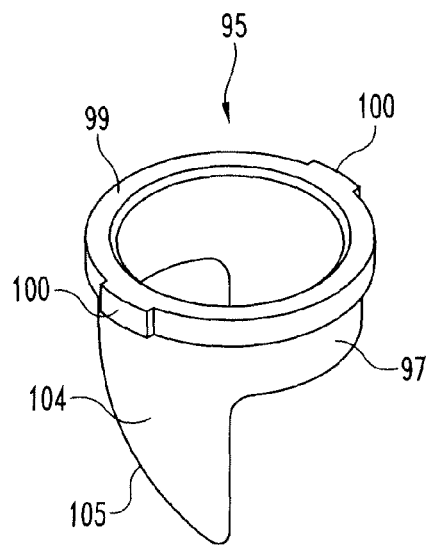
FIG. 7 is a perspective view of the driver of the delay mechanism of FIG. 1, which driver is shown separate from the other components.
Figure 8A:
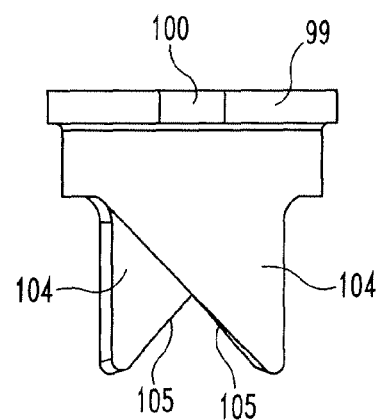
FIGS. 8A, 8B, and 8C are respectively front, side and top views of the driver of FIG. 7.
Figure 8B:
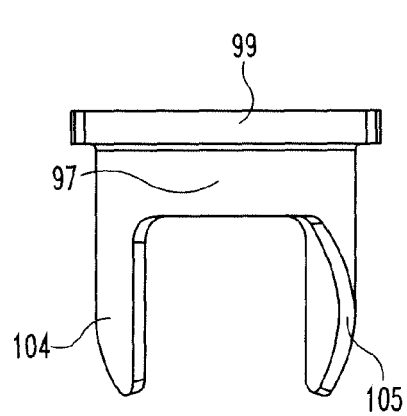
Figure 8C:
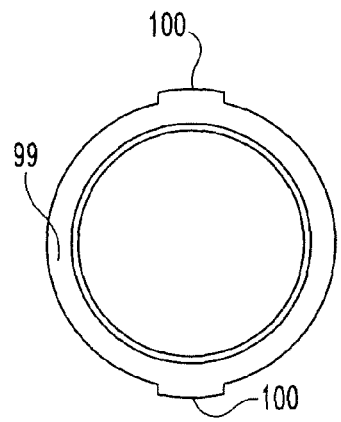

Referring now to FIGS. 1 and 2, there are respectively shown a front view and a partial, cross-sectional front view of an automatic injection apparatus equipped with a first embodiment of a delay mechanism of the present invention. As delay mechanisms of the present invention advantageously may be employed in a variety of differently configured automatic injection apparatuses, only limited injection apparatus details are shown and described herein, and such details are intended to be illustrative and not limiting in any way.

As is conventional, the automatic injection apparatus, generally designated 20, has a trigger that when actuated by a user results in the needled syringe of the apparatus being driven downward such that the injection needle projects beyond the bottom end of the apparatus housing to penetrate the user. The apparatus then proceeds to inject the medication contents of the syringe through the needle, after which the syringe is retracted such that the injection needle is returned to within the housing. The inventive delay mechanism shown helps to stage the operation of the apparatus to ensure that the medication contents are properly delivered prior to the needled syringe being retracted.

Apparatus 20 includes an outer housing 22 in which are operationally disposed working components of the apparatus. The main body 24 of housing 22 is shown as having a generally cylindrical-shaped exterior with a flared end 23, but may be differently shaped. Main body 24 extends between a proximal end 27 and a distal end 28. As used herein, distal and proximal refer to axial locations relative to an injection site when the apparatus is oriented for use at such site, whereby, for example, proximal end of the housing body refers to the housing body end that is closest to such injection site.

At the top or distal end of the housing, a safety-controlled button 25 that is part of the user-operated trigger is provided. When the safety sleeve 26 of the housing is disposed in a proper angular orientation relative to the housing body 24 as rotatably adjusted by the user, button 25 is unlocked and can be depressed to start the automatic injection function of the apparatus. The internal workings of the locking/triggering mechanism allowing the apparatus to be selectively triggered for operation by a user may be differently configured in ways that are known in the art. One locking/triggering mechanism for apparatus 20 that is particularly adapted for the inventive delay mechanism to limit the overall length of the apparatus is shown in FIGS. 20 and 21.

Figure 21:
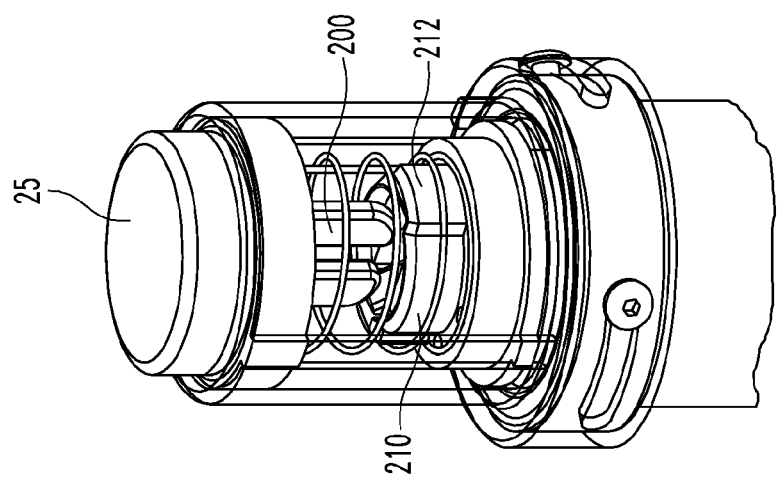
FIGS. 20 and 21 are partial perspective views, at different stages of operation, of the locking and triggering portion of the automatic injection apparatus of FIG. 1.
Figure 20:
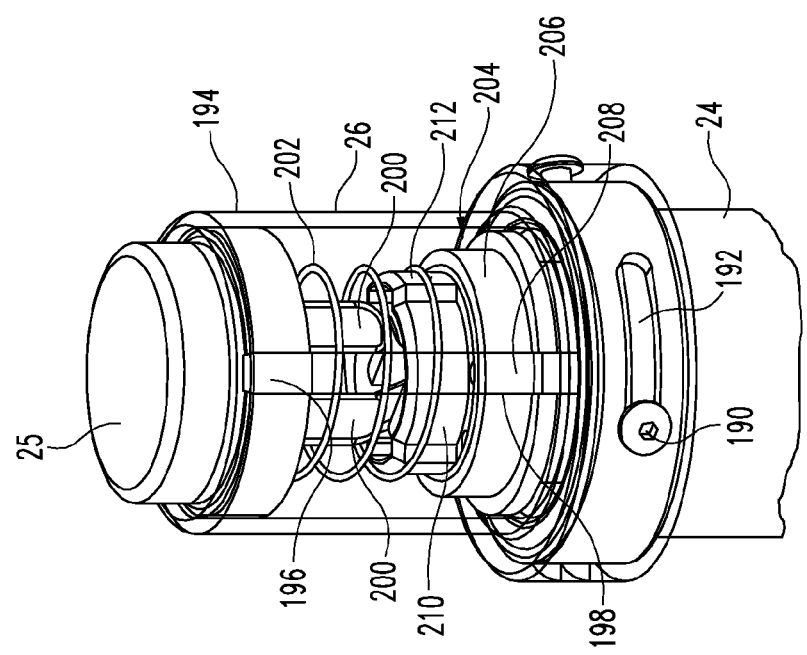

In FIGS. 20 and 21, the upper portion of the apparatus is shown at different stages of its operation, and with the housing safety sleeve 26 shown transparent to facilitate an understanding of the internal components. Safety sleeve 26 is diagrammatically shown rotatably mounted to the housing body 24 with its rotation limited by pins 190 attached to the housing and which slide within slots 192 of the sleeve. Button 25 includes an enlarged shoulder 194 that is captured within the interior of safety sleeve 26. Button 25 is rotatably fixed to sleeve 26 by a radially projecting rib 196 formed on button shoulder 194 which slides within a longitudinally extending notch 198 on the interior surface of sleeve 26. Depending from the underside of button 25 is a pair of radially aligned flanges 200 that engage prongs 41 of the plunger element 36. A coiled spring 202 is disposed between and urges apart the button 25 and a trigger lock, generally designated 204.

Trigger lock 204 includes an annular base 206 that includes a radially projecting rib 208 that slidably fits within notch 198 to rotatably fix the trigger lock with the sleeve 26. A collar 210 projects upwardly from base 206 and includes a pair of diametrically opposed collar sections 212 that are offset radially outward of the remainder of the collar 210.

When the locking/triggering mechanism is oriented as shown in FIG. 20, which orientation is also partially shown in FIG. 2, the apparatus is locked as the non-offset portion of collar 210 backs the radially outward faces of the plunger prongs 41 to prevent such prongs from splaying outward. If a user attempts to push button 25 downward, button flanges 200 abut shuttle flanges 76, which prevent further button depression. When the locking/triggering mechanism is rotated by the user into the configuration shown in FIG. 21, collar offset sections 212 are aligned radially outward of plunger prongs 41, and button flanges 200 are aligned over such prongs. In this unlocked state, when a user applies a plunging force on button 25, flanges 200 are shifted downward into a direct engagement of prongs 41, causing such prongs to splay outward, as they are not interfered with by collar sections 212, such that the plunger prongs can fit through the shuttle openings 74 as the plunger is biased downward.

Referring now to FIG. 2, apparatus 20 includes a medication-filled syringe, generally designed 30. Syringe 30 is of a generally standard design and includes a glass barrel 32 with an injection needle 34 mounted at its proximal end which is in fluid communication with the medication contents of the syringe barrel. The plunger mechanism of the syringe is formed in two parts by a plastic plunger element 36 and an elastomeric sealing member or piston 38 that seals the medication within barrel 32. The proximal region 40 of plunger element 36 serves to operationally abut sealing piston 38 during plunging and extends axially upward therefrom. The small gap shown provided between the element 36 and the piston 38 of the plunger is to allow for manufacturing tolerances and slight volume changes of the syringe contents, such as due to temperature changes, prior to use. The shown distal region of plunger element 36 includes a pair of prongs 41 adapted to latchably engage the shuttle until released by the apparatus triggering mechanism for the shown embodiment. A radially outwardly projecting, circumferential flange 42 of plunger element 36 serves as a shoulder against which acts the drive spring 44 of the apparatus.

Syringe 30 is mounted in a carriage 46 and biased or held up within a shuttle, generally designated 50, by a biasing spring 48 that acts between carriage 46 and the shuttle. When the apparatus is triggered, drive spring 44 drives plunger element 36 and thereby sealing member 38 proximally, which driven motion overcomes the force of spring 48 to shift syringe barrel 32 proximally relative to the shuttle and the housing 22 to cause the tip of needle 34 to project beyond housing proximal end 27 for penetrating a user's skin, and then forces the medication contents of the syringe through that needle for an injection.

Referring now to FIGS. 3 and 4A-4D, the shuttle of the first embodiment of the invention is shown in multiple views separate from the other device components. Shuttle 50 serves to latch with the follower of the delay mechanism, as well as serves to carry distally, or otherwise in another possible embodiment to allow distal motion of, the syringe when unlatched from the follower. Other shuttle configurations that provide this functionality may be substituted for the configuration shown within the scope of the invention.

Shuttle 50 is formed of two mating plastic parts 52 and 53 that are fixedly connected, such as with an adhesive, along a parting line 54. While this two piece forming facilitates molding and assembly of the plunger, different constructions may be employed. Shuttle 50 includes a tubular, cylindrical body 56 with at least one, and preferably a pair of diametrically opposed, longitudinally extending slots 58 formed through the wall of the body along a majority of its length. Slots 58 allow engagement of a locking member of the delay mechanism by the plunger during injection. As shown in FIG. 2, each slot 58 slidably receives a radially extending portion of the plunger in the shown embodiment, which plunger portions consist of a pair of projections 43 from plunger flange 42. Although the locking member is directly engaged by projections 43 of the plunger element part that supports a drive spring, other functional constructions are within the scope of the invention, including an indirect engagement of the locking member via an intervening part.

The shuttle also includes near its proximal end at least one, and preferably a pair of latching elements for releasably engaging the follower of the delay mechanism. The latching elements are provided as portions of a pair of diametrically opposed, L-shaped slots that are generally designated 60. The short track or leg 62 of the L-shaped slot 60 is oriented transverse to the longitudinal direction, and extends a limited distance around the shuttle body circumference. Slot leg 62, and more particularly the surface of the shuttle body that defines that slot portion and which defines an abutment for a projecting tab of the follower, provides a lock or latching element to engage the follower. The axially extending portion 64 of each slot 60 is the release path or track by which the shuttle is able to unlatch from the follower.

Although slot 60 is shown extending through the entire wall thickness of tubular body 56, the shuttle 50 may be equipped with differently configured latching elements within the scope of the invention. For example, the track could be replaced with a tab that cooperates with a complementary track on the follower. Still further, rather than a slot, an appropriately shaped groove or notch could be formed into the shuttle periphery, but such would necessitate a thicker and perhaps less desirable shuttle construction.

At its proximal end, shuttle 50 includes an annular lip 66 that extends radially inward of the shuttle body 56. The opening defined by lip 66 allows the syringe barrel 32 to extend therethrough. Lip 66 serves as a shoulder against which biasing spring 48 acts, and further is the load-bearing surface with effectively carries the syringe 30 distally during the step of retracting the needle 34 within the apparatus housing 22 after injection.

Distally of parting line 54, shuttle 50 includes a circumferentially extending flange 70 that projects radially outward from body 56. Flange 70 serves as a shoulder against which acts a biasing member used to shift shuttle 50 distally to power needle retraction. The biasing member is shown provided as a helically coiled spring 72 that is concentrically mounted around the shuttle body. Diametrically opposed ribs 79 projecting from flange 70 fit within not shown, complimentarily shaped grooves formed in the interior surface of housing body 24. These grooves extend longitudinally and are sized to rotatably lock the shuttle relative thereto and guide the axial movement of the shuttle during its retraction.

The distal end of shuttle 50 is shown as having an otherwise closed end 73 provided with a pair of spaced slots 74 that allow passage of the prongs 41 of the plunger. Closed end 73 serves as a seat on which the trigger lock 204 is rotatably disposed. Slots 74 define a span 75 of the shuttle closed end. Span 75 is latchable by the plunger prongs and is flanked by a pair of upstanding flanges 76 that prevent downward motion of the triggering button 25 when that button is in the locked state.

Referring now to FIGS. 5 and 6A-6C, the locking member of the first embodiment of the invention is shown in multiple views separate from the other device components. The locking member, generally designated 80, is molded in one piece from plastic and includes a tubular, cylindrical body or collar 82 that fits concentrically around shuttle body 56. The locking member also includes at least one, and preferably a pair of diametrically opposed keys or splines 84 that upwardly extend from the collar 82. Each spline 84 includes a radially inwardly extending tip portion 85 that projects within the radial space above the opening defined by collar 82 so as to fit within a shuttle slot 58 and rotatably fix together shuttle 50 and locking member 80. The outer radial face of each spline 84 includes a beveling 87, which facilitates latching with the follower, and a transverse groove 86. Longitudinal slots 90 formed in the collar 82 adjacent the splines 84 provide the splines with radial resiliency to allow, during manufacturing assembly, the locking member to releasably latch with the follower.

While the splines 84 are designed to rotatably engage the locking member 80 with both the shuttle 50 and the follower 110 as described below, different pieces of the locking member could provide the various engagements in alternate embodiments. In addition, although the spline tips portions 85 are axially positioned to be moved out of locking engagement by the plunger mechanism near the end of the apparatus plunger stroke, such a design is dependent on tolerances and results from an intent to unlock the locking member as near to the end of injection as possible. Different times of unlocking the locking member by the plunger during its stroke, such as closer to the beginning of the plunger stroke, may be accommodated within the scope of the invention, so long as the delay mechanism provides a suitable delay time for proper apparatus operation.

Referring now to FIGS. 7 and 8A-8C, the driver of the first embodiment of the invention is shown in multiple views separate from the other device components. The driver, generally designated 95, is molded in one piece from plastic and includes a tubular, cylindrical body or collar 97 that fits concentrically around shuttle body 56. A circumferentially extending lip 99 rings the distal end of body 97. Diametrically opposed ribs 100 that project radially outwardly from lip 99 slidably fit within the pair of not shown, longitudinally extending channels formed in the inner peripheral surface of housing body 24 to rotatably fix the driver 95 to the housing body 24. Downwardly depending from driver body 97 is at least one, and preferably a pair of diametrically opposed camming members or cams 104. The camming members 104 are shown as being generally ramp shaped, with the ramp camming surface 105 making an included angle relative to horizontal of approximately 45 degrees. This angle of the driver camming surface is selected in conjunction with that of the follower cammable surface in furtherance of providing a proper rate of rotation of the follower as described further below. Other forms of camming members than the ramp shape shown may be employed within the scope of the invention.

Driver 95 is urged proximally within the apparatus housing by a biasing member that directly engages the upper face of driver lip 99. Although in the shown embodiment that biasing member is shown as the coiled spring 72 that also biases shuttle 50 upward, a different type of biasing member may be used. In addition, a biasing member distinct from the spring that biases shuttle 50 may be used, although such would increase the number of parts required.

Referring now to FIGS. 9 and 10A-10E, the follower of the first embodiment of the invention is shown in multiple views separate from the other device components. The follower, generally designated 110, is molded in one piece from plastic and includes a tubular, cylindrical body or collar 112 that fits concentrically around shuttle body 56 at a location proximal of driver 95. Upwardly extending from follower body 112 is at least one, and preferably a pair of diametrically opposed cammable members 114. Cammable members 114 are shown as being generally ramp shaped, with the cammable surface 115 that slidably engages a camming surface 105 making an included angle relative to horizontal of approximately 45 degrees.

Figure 10D:
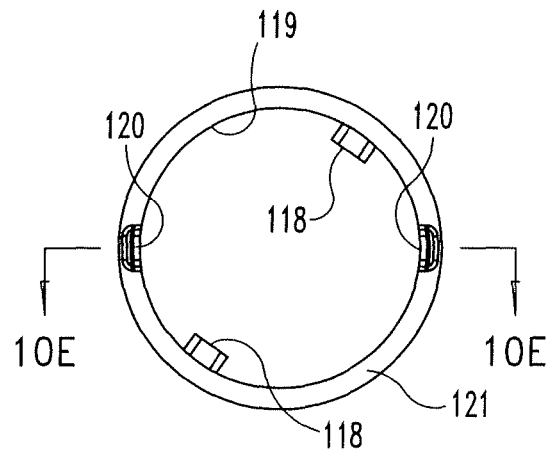
Figure 10E:
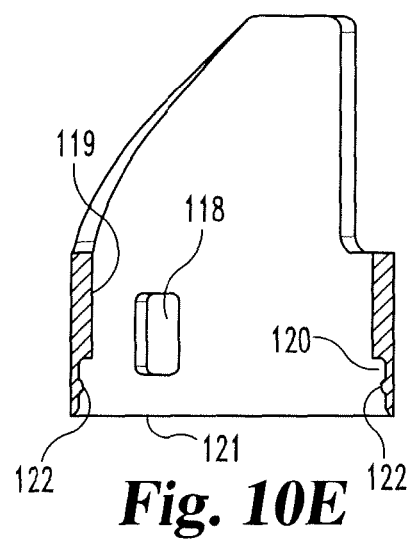
Figure 11:
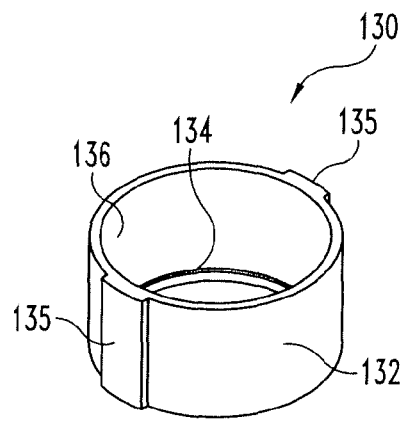
FIG. 11 is a perspective view of the grease collar of the delay mechanism of FIG. 1, which grease collar is shown separate from the other components.
Figure 12A:
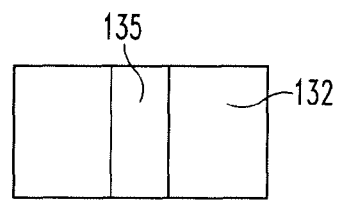
FIGS. 12A, 12B, and 12C are respectively front, side and top views of the grease collar of FIG. 11.
Figure 12B:
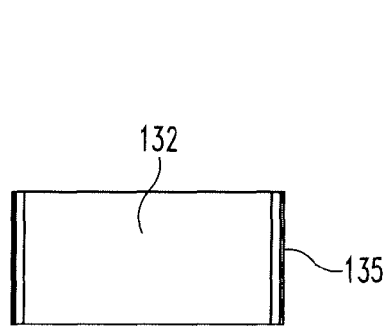
Figure 12C:
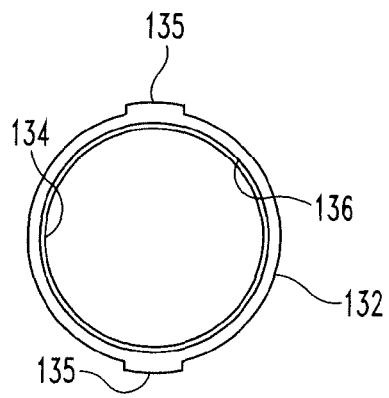
Figure 13:
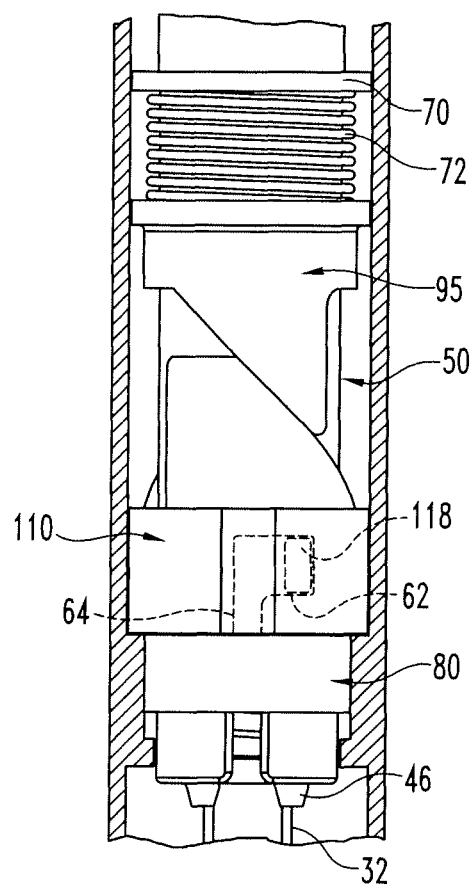
FIGS. 13, 14, 15 and 16 are partial front views, in partial cross-section, of the apparatus of FIG. 1 at various stages of its operation.
Figure 14:
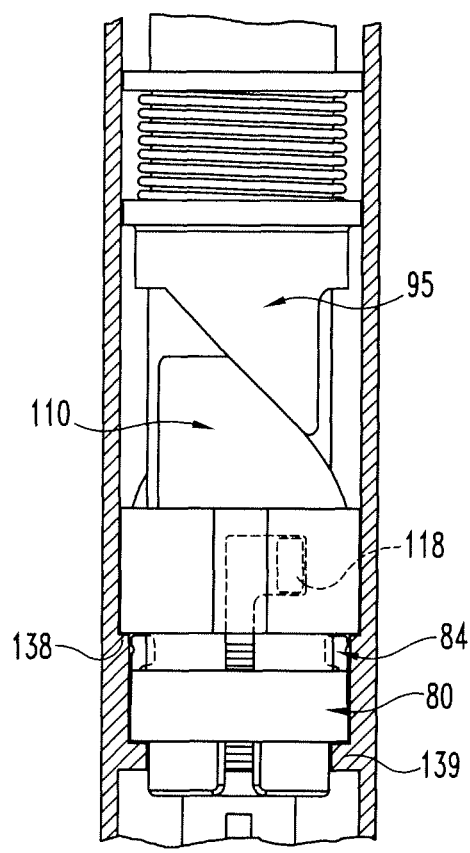
Figure 15:
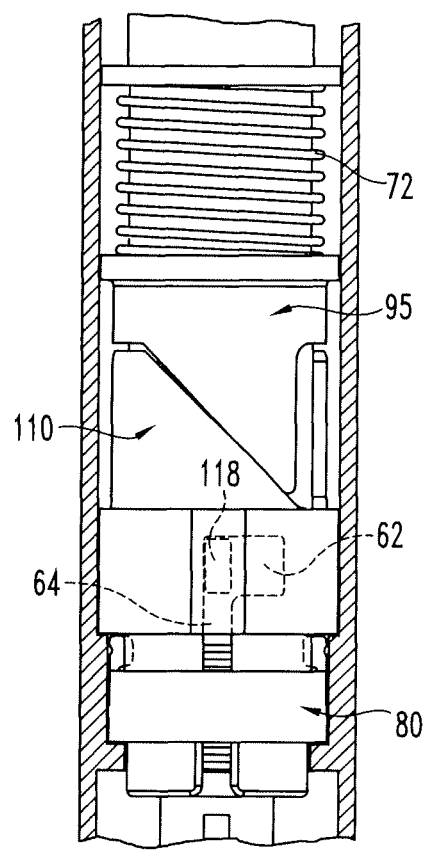
Figure 16:
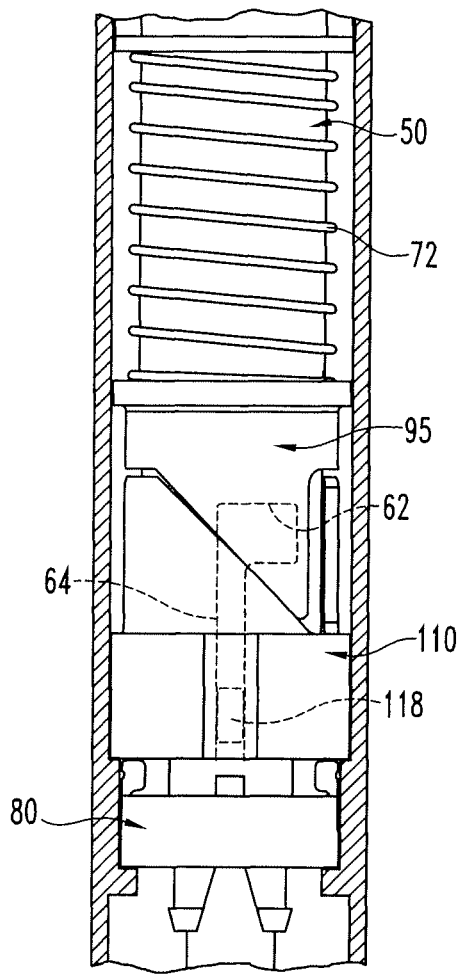

Follower 110 includes a pair of diametrically opposed blocks or tabs 118 that project radially inwardly from an interior surface 119 of the body 112. Blocks 118 serve as latching elements and fit within the shuttle L-shaped slot 60 for controlling operation thereof. A pair of diametrically opposed notches 120 is formed into the inner interior surface 119 along the bottom face 121 of follower body 112. Locking member keys 84 fit within notches 120 to rotatably lock the follower 110 to the locking member 80. As shown in FIG. 10E, a transverse rib 122 is provided within each notch 120. Each transverse rib 122 fits within groove 86 to releasably, axially latch together follower 110 and locking member 80. This releasable latching holds the components together until the locking member 80 is positively pushed downward by the syringe plunger during operation to unlock the components and allow rotation of the follower 110.

The forced rotation of follower 110 is dampened to provide the proper delay period to ensure the plunger stroke is sufficiently complete before needle retraction. The preferred damping technique uses a viscous compound disposed radially, but not axially, between the follower 110 and a support surface relative to which the follower rotates. A larger axial height of the viscous compound interface between the follower and support surface improves tunability and consistency of the delay function.

Referring now to FIGS. 11 and 12A-12C, a grease collar that provides this support surface in the first embodiment of the invention is shown in multiple views separate from the other device components. The grease collar, generally designated 130, is molded in one piece from plastic and includes a tubular, cylindrical body 132 that fits concentrically around follower 110. A lip 134 extends radially inwardly and rings the inner circumference of body 132 at its proximal end. Lip 134 is abutted by the bottom face 121 of follower body 112, and the proximal face of collar body 132 abuts housing rib 138, thereby preventing both the follower 110 and grease collar 130 from moving proximally in housing body 24. The collar body 132 includes a pair of diametrically opposed, radially projecting ribs 135 that are held within the not shown housing channels so as to rotatably fix grease collar 130 within the housing body 24.

The damping compound support surface of grease collar body 132 is its inner radial periphery indicated at 136. Grease collar 130 can be eliminated in other embodiments in which the viscous damping compound is placed directly between the follower and a different fluid supporting surface, for example, a surface of housing body 24 or the shuttle or the driver. However, grease collar 130 facilitates assembly of the delay mechanism as well as allows for tolerance control such that the radial clearance in which the viscous compound is provided is readily controllable so as to be adjustable during the manufacturing tuning process.

Although not shown, and in order to further enhance such tolerance control between the follower 110 and the collar 130, the follower may be provided with flexures, such as in the form of a plurality of, such as four, evenly circumferentially spaced, longitudinally extending slots in the follower body 112 which extend upward from the follower bottom face 121.

The damping compound, indicated at 140 in FIG. 2, is disposed between collar surface 136 and the outer radial periphery 113 of follower body 112. One suitable compound is fluorocarbon gel 836A available from Nye Lubricants in Fairhaven, Mass., which has a kinematic viscosity that varies with temperature, with one data point being 10000 centistokes at 40 degrees Celsius. This compound is suitable for a delay mechanism having to provide consistent delay times across a wide range of use temperatures.

Other compounds with different properties may be selected by one of skill in the art in view of the delay selected by the manufacturer to be provided by the delay mechanism, and in view of modifications that may be made by the skilled artisan to the placement of the compound as well as other aspects of the delay mechanism. For instance, the resistance to rotation of the follower caused by the action of a damping compound will be affected by the surface area of compound application, and radial clearance. And, the time delay resulting from the mechanism follower having to overcome this resistance is a function of the angle of the driver/follower camming surfaces, the total angle swept by the follower, and the force applied to the follower, which force is a function of the spring force on the driver.

Still further, and rather than simply making minor modifications to the shown delay mechanism components, different types of damping mechanisms may be employed within the scope of the invention. For instance, a sealed chamber that holds a fluid displaced by an apertured piston type member associated with the follower may be used in place of the shown mechanism that depends on shearing of the damping compound to provide the resistance on the follower.

The construction of the inventive delay mechanism shown in FIGS. 2-12 will be further understood in view of a description of an operation of apparatus 20 with reference to FIGS. 2 and 13-16. With the apparatus initially configured as in FIGS. 2 and 13, and when the apparatus trigger button is then unlocked and depressed by a user, plunger prongs 41 are splayed out of latching engagement with shuttle span 75 and pass through slots 74 as plunger element 36 is driven proximally by drive spring 44. This proximal motion of plunger element 36, and the resulting proximal motion of plunger sealing member 38, first causes the syringe barrel 30 and needle 34 to shift, against a small force of the compressing spring 48, such that the injection tip of needle 34 protrudes beyond the housing body proximal end 27, and then continued plunger motion slides the plunger sealing member 38 proximally within the syringe barrel 30 to force the syringe contents through the needle. As plunger element 36 moves proximally, its projections 43 that slide within shuttle slots 58 reach and drive downward spline tip portions 85, overcoming the latching engagement of the spline grooves 86 and follower ribs 122 to force locking member 80 from its first axial position, at which it rotationally locks the follower, to a more proximal axial position in which splines 84 are clear from the follower notches 120 so as to unlock the follower for rotation. Housing rib 139 provides a ledge that prevents locking member 80 from moving too far proximally. At this point, the apparatus is configured as in FIG. 14.

Upon the unlocking of follower 110, the urging by spring 72 of driver 95 axially in the proximal direction within housing body 24 causes follower 110, due to the sliding of its camming surfaces 105 along cammable surfaces 115, to rotate within the housing and around the shuttle 50. The damping compound 140 between the follower 110 and grease collar 130 dampens or offers a resisting force to this follower rotation. Rotation of follower 110 about shuttle 50 is driven by the continued axial motion of driver 95 until tabs 118 have slid the length of the transverse tracks 62 in which they respectively ride to a point each in alignment with a release portion 64 of a slot 60. At this point, the apparatus is configured as in FIG. 15.

When tabs 118 are so aligned with slot portions 64, the shuttle 50 and follower 110 are effectively unlatched, allowing the shuttle 50, under the force of spring 72, to automatically and quickly shift distally, with tabs 118 sliding axially through slot portions 64, and carry the needled syringe 30 distally so as to retract the proximal tip of the injection needle 34 to a protected position within the housing 24. Shuttle 50 retracts until its engagement with the housing prevents further motion. During this shuttle motion, trigger lock 204 can be carried distally, against the force of spring 202 which compresses, by shuttle 50 within housing sleeve 26. At this point, the apparatus is configured as in FIG. 16, and after which the user can dispose or otherwise handle the apparatus in the normal course.

Figure 19:
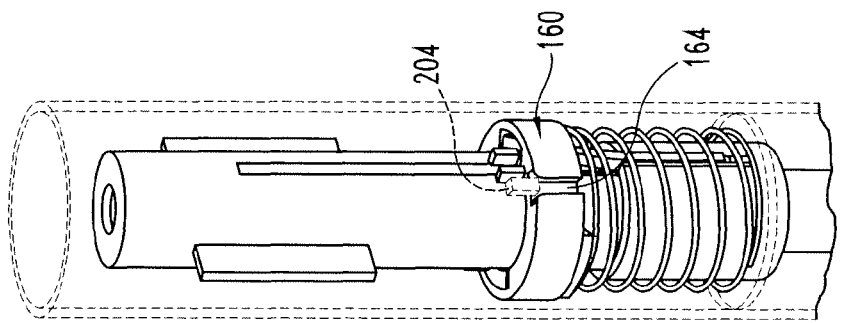
FIGS. 17, 18 and 19 are partial, diagrammatic perspective views of an injection apparatus with another embodiment of a delay mechanism of the present invention at different stages of its operation.
Figure 18:
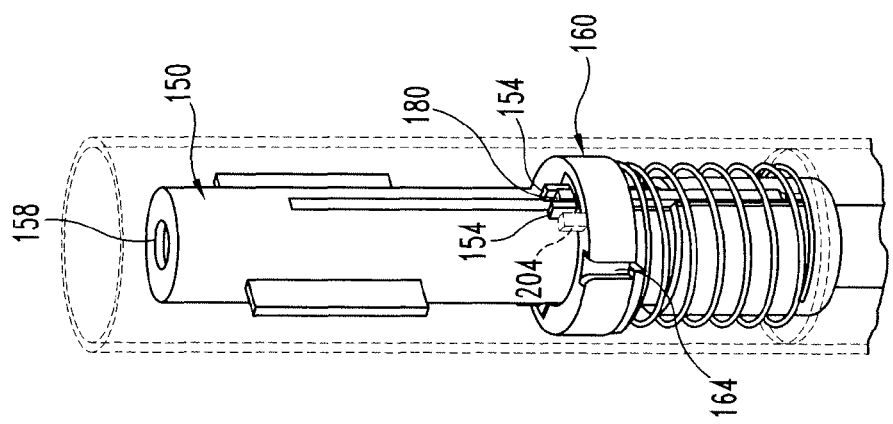
Figure 17:
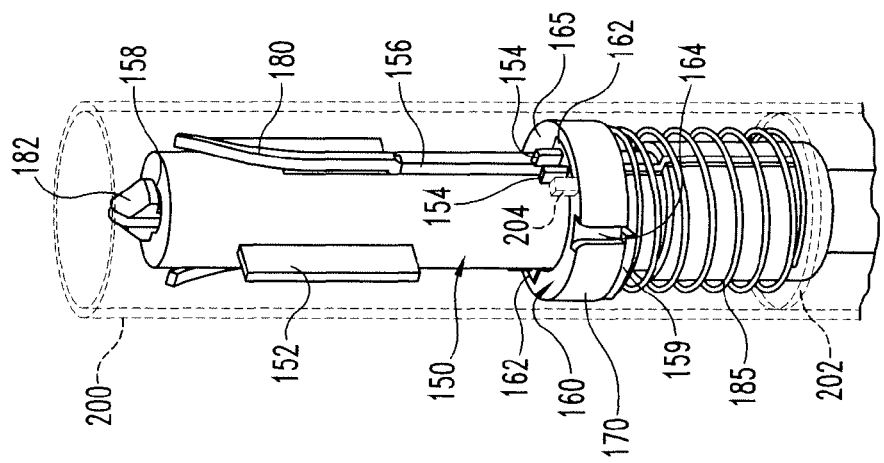

Referring now to FIGS. 17-19, there is shown another embodiment of a delay mechanism of the present invention within an automatic injection apparatus shown only partially and in shadow. The delay mechanism includes a shuttle 150, a follower collar 160, a damping compound 170, and at least one resilient finger 180 associated with the plunger.

Shuttle 150 is rotatably locked and axially movable within the housing 200 via a pair of flanges 152 that fit within not shown, longitudinally extending channels of the housing. A pair of straightening ribs 154 that are formed on the shuttle exterior periphery flank each longitudinal slot 156 near a central length portion thereof. The underside of a radially projecting flange 159 of shuttle 150 is acted upon by a biasing spring 185 that abuts a shoulder 202 of housing 200 at its opposite end. Flange 159 extends only partially around the shuttle circumference so as to be clear of a stop block 204 described below.

Collar 160 is disposed axially above shuttle flange 159 and extends around shuttle 150. Collar 160 includes a pair of notches 162 extending along its height at diametrically opposed portions of its inner radial periphery. Notches 162 are angularly aligned with shuttle slot 156 in FIG. 15. When the collar 160 is so aligned, the upper face 165 of collar abuts a stop block 204 formed on and projecting from the inner surface of housing 200. At least one other notch 164 is formed along the outer radial periphery of collar 160, which notch is not angularly aligned with stop block 204 when the components are oriented as shown in FIG. 17.

Damping compound 170 is provided around the circumference of collar 160 and is disposed between the outer radial periphery of collar 160 and an interior surface of the housing. Damping compound 170 acts between the housing and the collar to prevent the collar from freely spinning within the housing 200.

A pair of resilient fingers 180 extends along the outside of the shuttle and when in a neutral state are each angled from the shuttle slots 156. Fingers 180 are formed or otherwise connected with the plunger so as to extend through shuttle slots 156. The needled syringe carried by shuttle 150 is generally similar to that shown with respect to apparatus 20, although the plunger element prongs 182 are shown extending through a single, central hole 158 of the shuttle.

During apparatus operation, and with the apparatus initially configured as in FIG. 17, when the syringe plunger is driven proximally or downward by the drive spring acting on the plunger within the shuttle interior, the resilient fingers 180 are forced to straighten, thereby storing energy, as they pass between straightening ribs 154 and into notches 162. This finger straightening process is shown in FIG. 18. When the plunger has neared the end of its stroke, the fingers 180 move free of and are released from the ribs 154 and exert a force on collar 160. This force causes collar 160 to rotate against friction provided by the damping compound. When the collar 160 has rotated sufficiently such that notch 164 has moved into angular alignment with stop block 204 as shown in FIG. 19, the collar and the shuttle are effectively unlocked with respect to the housing so as to be moved distally under the force of spring 185 as block 204 in effect passes through notch 164, which shuttle movement thereby retracts the syringe so that the syringe needle is retracted inside the housing.

Figure 22:
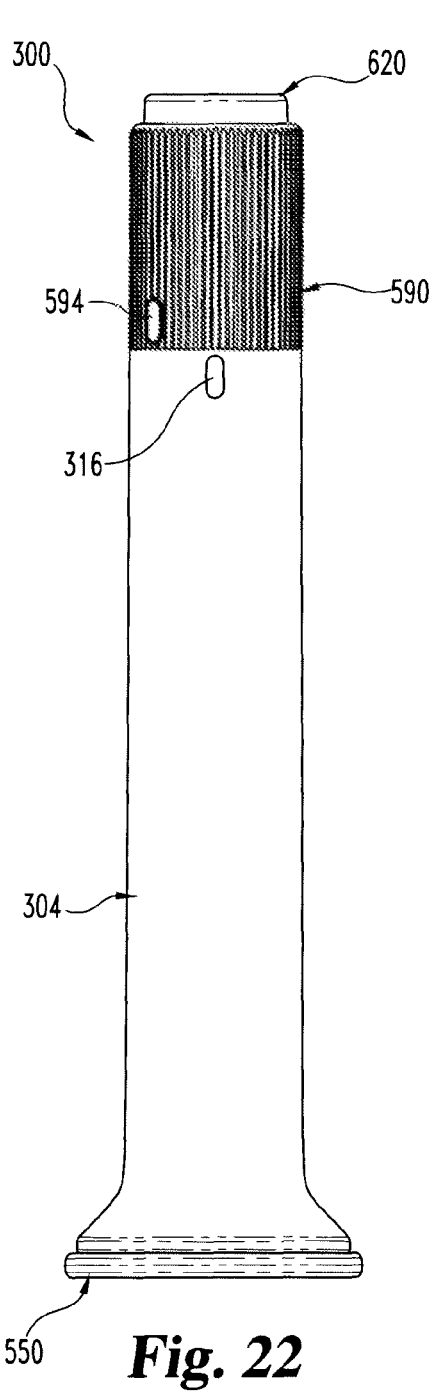
FIG. 22 is a front view of an automatic injection apparatus equipped with still another embodiment of a delay mechanism of the present invention.
Figure 23:
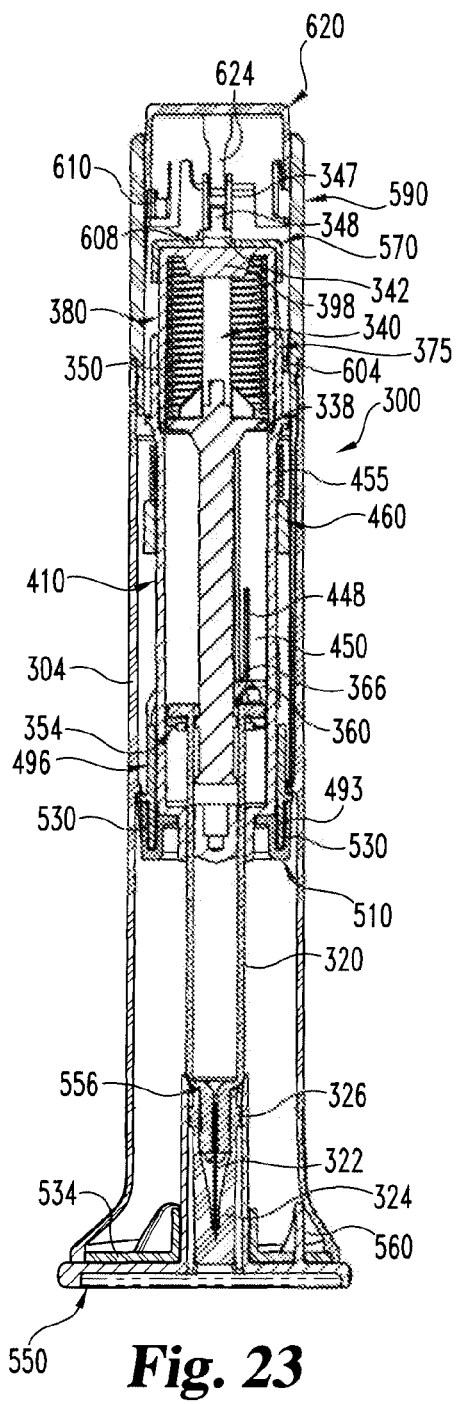
FIG. 23 is a front view, in longitudinal cross section, of the automatic injection apparatus with inventive delay mechanism of FIG. 22, at which point the apparatus is in a ready to use arrangement in which it has yet to be uncapped for use.

Referring now to FIGS. 22 and 23, there are respectively shown a front view and a longitudinal cross-sectional view of an automatic injection apparatus equipped with still another embodiment of a delay mechanism of the present invention. The automatic injection apparatus, generally designated 300, is related to the apparatus 20 in overall concept as will be recognized by one of skill in the art, but is different in both its physical configuration and its operation as described more fully below.

As further shown in FIGS. 24A-C, the outer housing includes a tubular body 304 formed of an ABS Plastic, such as Polylac PA-758 available from Chi Mei Corporation. Body 304 is transparent and has a generally cylindrical-shaped exterior having a flaring 306 at its proximal end. Near a middle length portion of housing body 304, a pair of circumferentially spaced ridges or stops 308 are formed on the body interior surface for supporting the damping collar 510. Each ridge 308 includes a distally projecting key 309 located along its angular length. A second set of circumferentially spaced ridges 310 angularly offset from stops 308 and located distally thereof serve to axially locate the follower 475. Near the housing body distal end, a circumferential or annular snap ring 312 projects inwardly from the housing body interior surface. A pair of longitudinally extending and diametrically opposed ridges 314 projects from the body interior surface proximally of snap ring 312. An alignment marking 316 is shown pad printed on the outer periphery of housing body 304 near its distal end.

Figure 25:
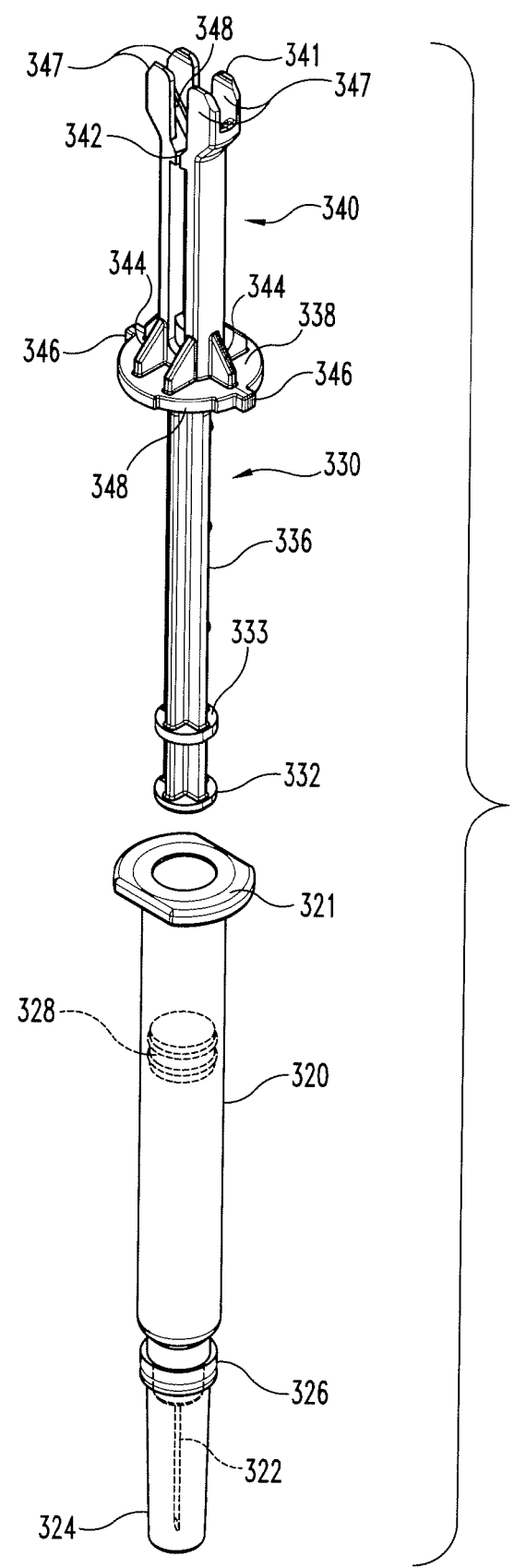
FIG. 25 is an exploded perspective view of the syringe and plunger of the apparatus of FIG. 22 shown separate from the other apparatus components.

As further shown in FIG. 25, the medication-filled syringe used in the apparatus includes a glass barrel 320 with an injection needle 322. An elastomeric needle shield 324 with a protruding, circumferential rib 326 fits to the syringe barrel over the needle 322 for sterility purposes. The plunger mechanism of the syringe is formed in two parts by a plunger element 330 and an elastomeric piston 328 that seals the medication within the tubular barrel 320.

Plunger element 330 is formed of ABS plastic and includes a piston engaging foot portion 332, a cruciform-shaped stem 336 extending up from foot-portion 332 and ending at a radially outwardly projecting, disc-shaped flange 338, and a pair of resilient arms or prongs 340 projecting upward from flange 338. A flange formed along stem 336 serves as a ledge 333 engageable with the syringe carrier. Flange 338 serves as a shoulder against which acts the drive spring 350 of the apparatus. A series of gussets 344 extend between flange 338 and the prongs 340 to add rigidity as well as center the spring 350. Other gussets between flange 338 and stem 336 further add rigidity. Flange 338 includes a pair of key tabs 346 radially projecting outward from the edge of flange 338 at locations spaced one hundred eighty degrees apart. A pair of similarly spaced notches 348 formed in the outer edge of flange 338 accommodates shuttle shift arms 446.

Figure 26A:
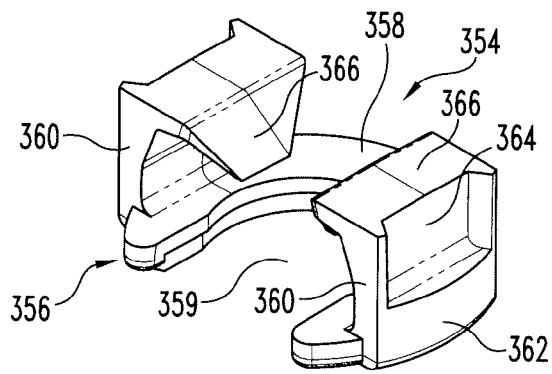
FIGS. 26A, 26B and 26C are respectively a perspective, proximal end, and elevational views of the overmolded syringe carrier of the apparatus of FIG. 22 shown separate from the other apparatus components.
Figure 26B:
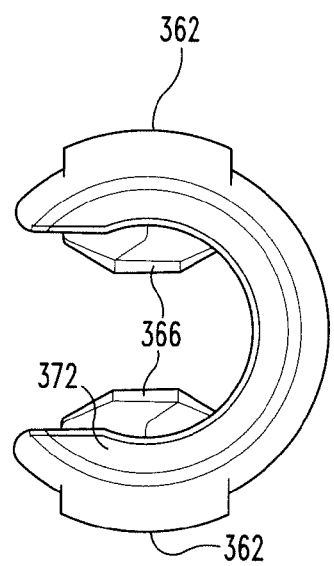
Figure 26C:
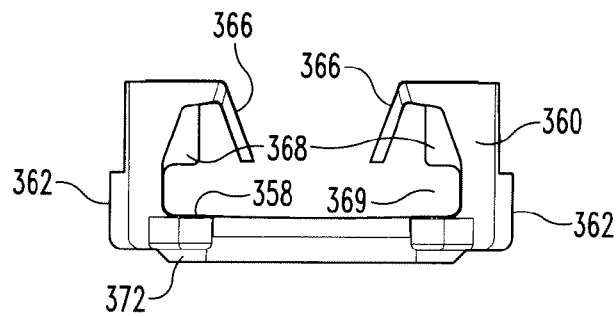
Figure 27A:
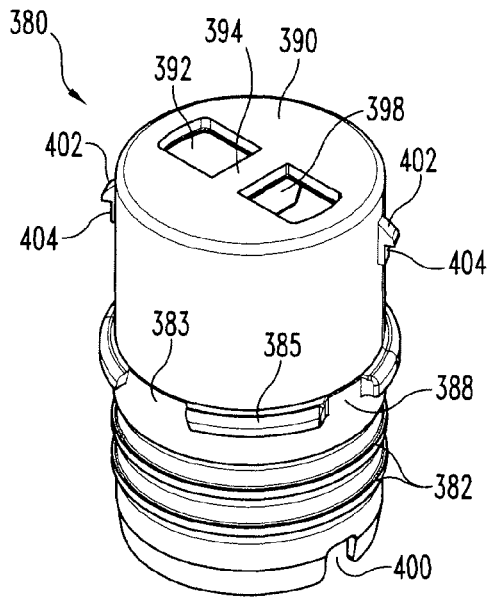
FIGS. 27A, 27B, 27C and 27D are respectively a top perspective, bottom perspective, longitudinal cross-sectional, and distal end views of the upper piece of the shuttle of the apparatus of FIG. 22 shown separate from the other apparatus components.
Figure 27B:
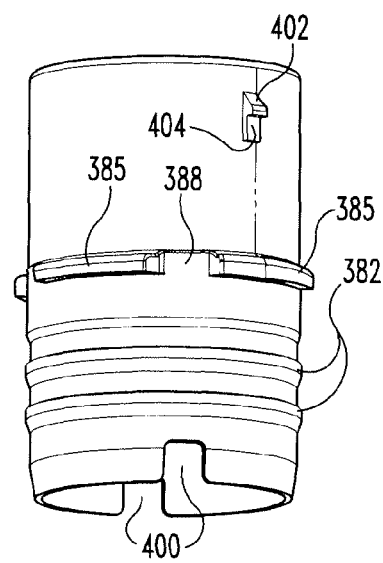
Figure 27C:
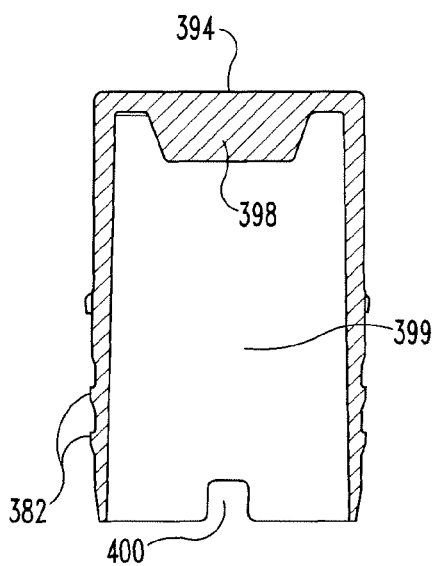
Figure 27D:
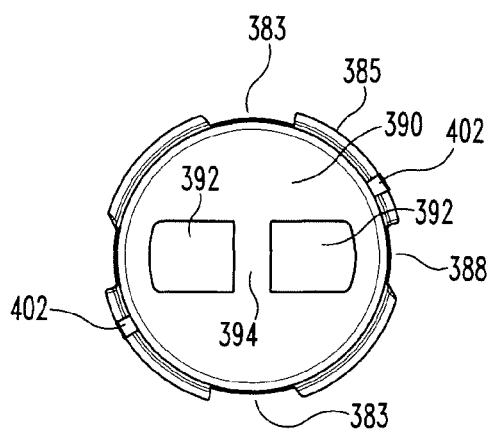
Figure 28A:
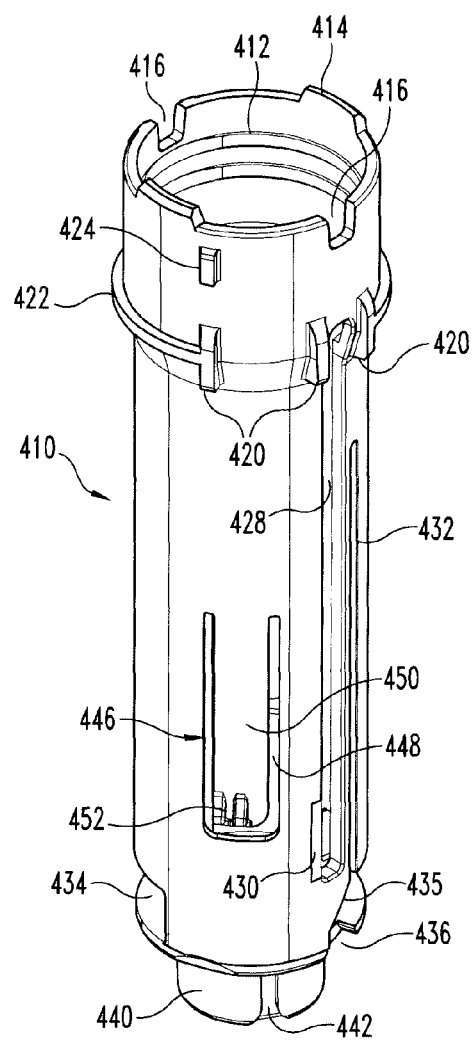
Figure 28B:
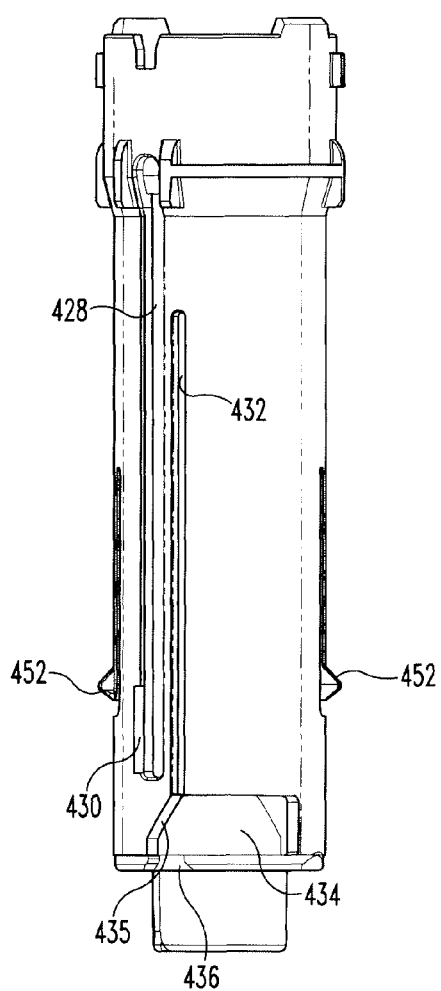
Figures 28E, 28F:
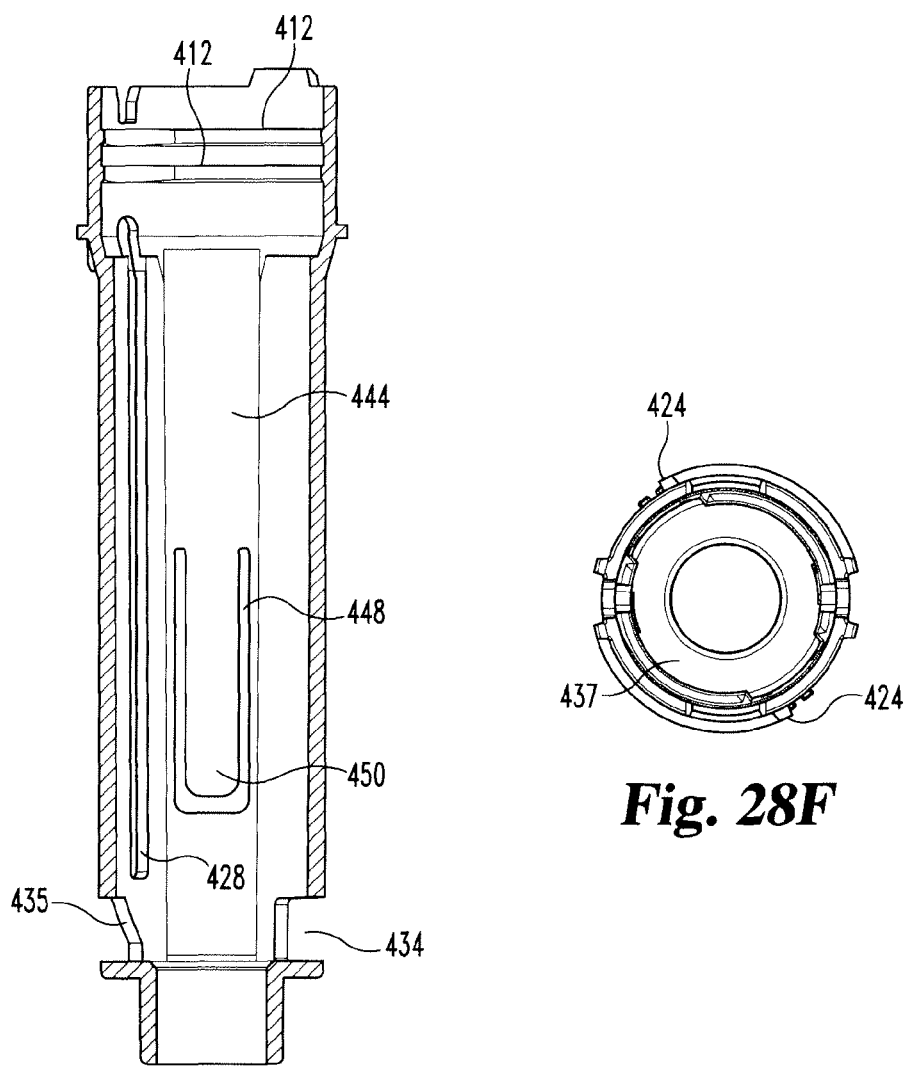

An overmolded syringe carrier further shown in FIGS. 26A-C is generally designated 354 and fits to the keyed flange 321 of syringe barrel 320 to be rotatably fixed together. Syringe carrier 354 includes a base 356 formed of ABS Plastic, which base includes a C-shaped ledge section 358 from which upwardly project a pair of supports 360 that have radially protruding portions 362. Portions 362 serve as shuttle keys for the syringe carrier, thereby rotatably fixing assembly 354 with the shuttle, as well as back up the shuttle shift arms described below when the apparatus 300 is in a ready to use arrangement. The syringe barrel 320 extends through the central opening 359 formed by ledge section 358. Each support 360 includes a notch that forms a shuttle shift arm accommodating hollow 364 as described below. The base 356 also includes plunger clips 366 that extend radially inward from supports 360. Plunger clips 366 are sized to engage the distal face of ledge 333 after the syringe and syringe carrier are shifted a short distance proximally during overcap removal described below. This engagement halts that syringe shifting and prevents the syringe, during overcap removal, from further shifting to a point at which the needle 322 temporarily projects beyond the proximal end of the apparatus housing 304. Each support 360 also includes a shoulder 368 that projects above ledge section 358 to define a space 369 in which barrel flange 321 is axially retained. The syringe carrier 354 further includes a landing pad 372 provided by overmolding a layer of a Shore 40A hardness thermoplastic elastomer over a portion of the underside of ledge section 358, which layer cushions the contact with the shuttle during use. In the ready to use arrangement of the apparatus 300 shown in FIG. 23, syringe carrier 354, via the associated syringe that abuts the overcap 550, is properly axially positioned for its shuttle shift arm backing function by the overcap that is detented into position with the housing base plate.

A shuttle of apparatus 300 which is assembled during manufacture around other apparatus components is formed from an upper piece 380 and a lower piece 410. Shuttle pieces 380 and 410, further shown in FIGS. 27A-D and FIGS. 28A-F, respectively, are made of a transparent ABS plastic. The assembled shuttle is generally referenced as 375.

Shuttle pieces 380 and 410 are fixedly connected via a snap fit connection using a pair of axially spaced annular ridges or snap rings 382 on the outer cylindrical periphery of shuttle piece 380 that seat within a pair of grooves formed by partial annular ribs 412 on the inner periphery of lower shuttle piece 410. A pair of diametrically opposed alignment dogs 414 projecting from the distal edge of piece 410 closely fit into gaps 383 in an annular flange 385 of shuttle piece 380 to ensure an aligned fixed rotational securement. A pair of notches or gaps 388 in flange 385 provides clearance for the trigger lock rotation nubs 606 during the upward motion of the shuttle during automatic needle retraction after the injection. The distal face 390 of upper piece 380 is closed but for a pair of windows 392 formed therethrough, which windows are aligned along the piece diameter and are spaced by an activation ledge or span 394 portion of the distal face. From the upper interior surface of upper piece 380, a tapered flange 398 depends in alignment with activation ledge 394 in the internal volume 399 in which is disposed the distal end of the drive spring 350, which flange strengthens ledge 394. Each window 392 allows the distal end 341 of a different resilient arm 340 to project from within volume 399. Facing activation hooks 342 integrally formed with and inwardly extending from the plunger arms 340 abut activation ledge 394 to hold the plunger element 330 axially relative to the shuttle when so latched. A pair of notches 400 formed in the proximal edge of piece 410 accommodates plunger tabs 346. Near the distal end of the shuttle piece, a pair of protrusions including both a retention tab portion 402, with a camming distal face, and a detent nub portion 404 are spaced 180 degrees apart on the shuttle exterior periphery.

Shuttle lower piece 410 is generally a stepped tubular sleeve in overall shape and includes diametrically opposed notches 416 in its distal edge. Notches 416 accommodate trigger lock rotation nubs 606 at the end of the shuttle retraction stroke after injection to thereafter rotatably fix the trigger locking sleeve 590 with the shuttle 375. A series of ribs 420 that are partially connected by ribs 422 serve as bearing surfaces for locking sleeve 590 A pair of lock ribs 424 for selectively preventing rotation of the locking sleeve 590 are spaced 180 degrees apart on the lower piece exterior periphery. A pair of diametrically opposed, longitudinally extending slots 428 formed through the wall of the shuttle lower piece 410 slidably receive plunger tabs 346 that unlock the locking members of the delay mechanism during injection. Along the proximal end region of each slot 428, a depression 430 is formed in the exterior periphery of lower piece 410 which serves as a ledge for one of the lock members. Depressions 430 set the radial release point of the lock members, which points are sub-flush as plunger tabs 346 do not extend radially outside of the outside surface of the shuttle lower piece to avoid interference with the driver 460 and follower 475during plunger motion. Closely angularly spaced with each slot 428 is a driver alignment channel or groove 432 formed into the exterior periphery of lower piece 410. Channels 432 extend longitudinally upward from separate apertures 434 and above retraction or release slots 436 formed in the annular lip 437 of lower piece 410. The surfaces defining apertures 434 serve as latching elements for releasably latching the delay mechanism follower. Apertures 434 are of sufficient axial height in view of the follower retraction blocks 486 to allow small axial shifting of shuttle 375 relative to the follower 475 required to allow unlocking of the locking sleeve as described below. A corner of each aperture 434 is angled at 435 in alignment with a slot 436 and assists assembly. A reduced diameter sleeve portion 440 of lower piece 410 which extends downward from annular lip 437 provides a syringe bearing neck. Axial extending channels or keyways 442 provided in the exterior of sleeve portion 440 fit with alignment keys or ribs of the damping collar 5 10.

Two shuttle shift arms involved in the staging of apparatus triggering are generally designated 446. Shift arms 446 are formed by U-shaped slots 448 formed in diametrically opposed portions of the shuttle lower piece, which slots 448 define fingers 450 that are resilient due to the shuttle construction. Each finger 450 is aligned with a different syringe carrier channel 444 that longitudinally extends within the inner periphery of shuttle lower piece 410. Near the proximal end of each finger 450, on its outer radial periphery, radial protrusions 452 are provided.

The shuttle biasing member is shown in FIG. 23 provided as a helically coiled metal spring 455 is concentrically mounted therearound. The distal end of spring 455 abuts the proximal end faces of lower ribs 420, while the proximal end of spring 455 abuts driver distal edge 464. Spring 455 is involved in the delay mechanism, as well as serves as the biasing member used to power the syringe retraction.

Figure 29A:
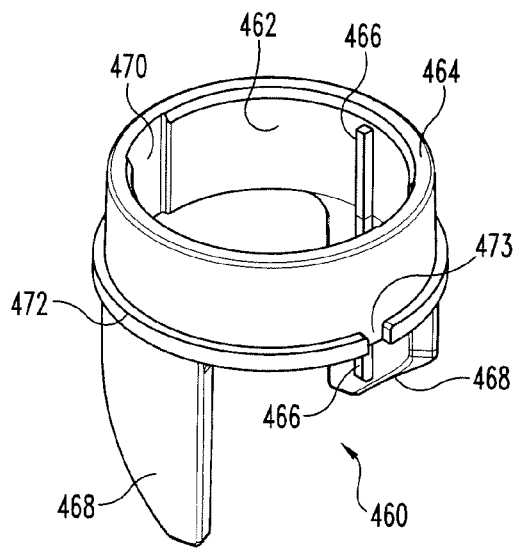
FIGS. 29A, 29B and 29C are respectively a perspective, distal end, and elevational views of the driver of the apparatus of FIG. 22 shown separate from the other apparatus components.
Figure 29B:
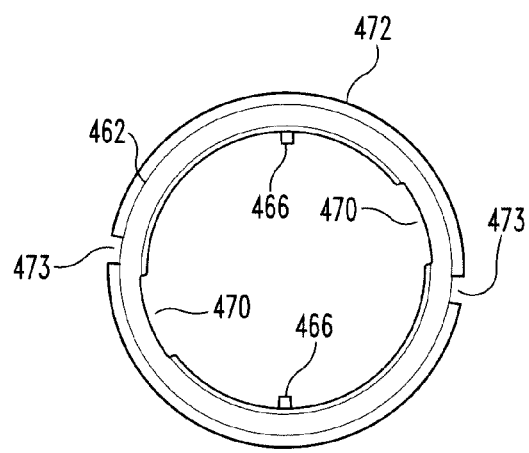
Figure 29C:
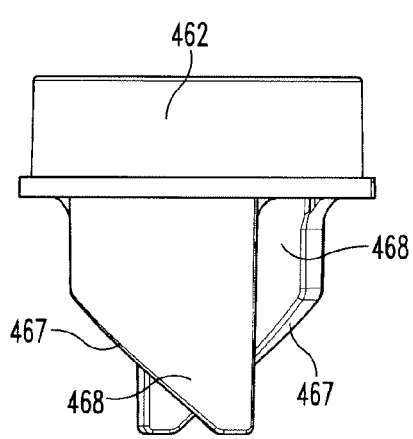
Figure 30A:
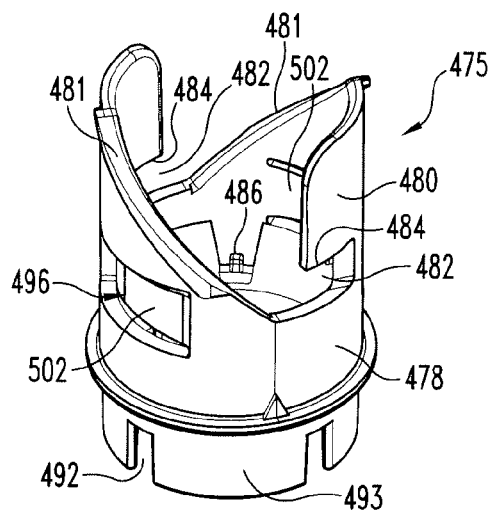
FIGS. 30A, 30B, 30C, 30D and 30E are respectively a top perspective, first and second elevational, a longitudinal cross-sectional, and distal end views of the follower of the apparatus of FIG. 22 shown separate from the other apparatus components.
Figure 30B:
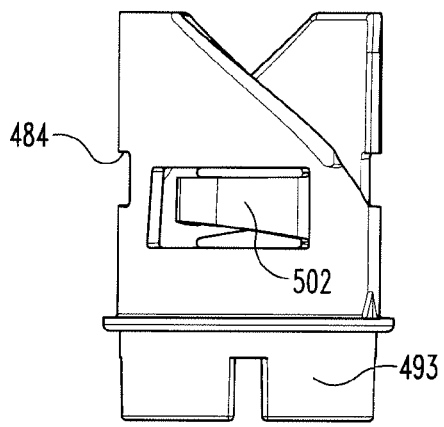
Figure 30C:
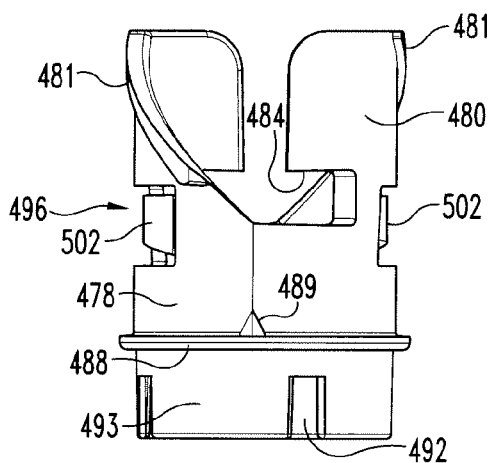
Figure 30D:
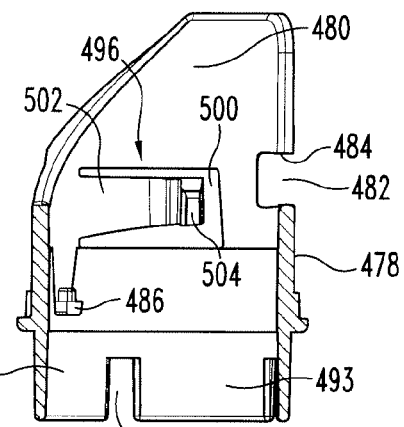
Figure 30E:
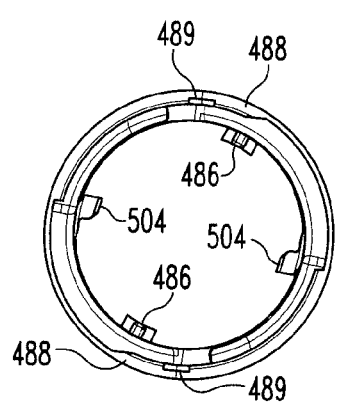

As further shown in FIGS. 29A-C, the delay mechanism driver, generally designated 460, is molded from ABS plastic and includes a tubular, cylindrical body 462 that fits concentrically around shuttle lower piece 410. Downwardly depending from driver body 462 is a pair of diametrically opposed, ramp-shaped cams 468. Diametrically opposed, longitudinally extending ribs 466 that project radially inwardly from body 462 and cams 468 slidably fit within shuttle channels 432 to rotatably fix the driver and shuttle together. A circumferential flange 472 with a pair of keyways 473 are provided on body 462. Keyways 473 accommodate housing ridges 314 to further directly rotatably fix the driver and housing together. Driver body 462 also includes a pair of internal channels 470 to allow clearance for shuttle shift arms 446.

As further shown in FIGS. 30A-E, the follower, generally designated 475 includes a tubular, cylindrical body 478 that fits concentrically around shuttle lower piece 410 proximally of driver 460. Follower 475 is molded from a suitable material, such as Delrin® POM Grade 500P NC010 available from Dupont. A pair of diametrically opposed, generally ramp-shaped cammable members 480 upwardly extend from follower body 478. Each member 480 includes a lip 481 that increases the diameter and area of the cammable surface of the member which slidably engages the camming surfaces 467 of the driver. A transversely extending notch 482 that is formed in the trailing edge of each cammable member 480 forms a jam ledge 484 for the radial protrusions 452 of shuttle shift arms 446. When apparatus 300 is provided to a user in its ready to use arrangement shown in FIGS. 22 and 23, shuttle 375 is axially fixed to follower 475 in a proximal location due to the engagement of shuttle shift arm protrusions 452 with jam ledges 484. Shuttle protrusions 452 fit therein due to shift arm fingers 450 being forced radially outward by the syringe carrier protruding portions 362 that radially back up the proximal ends of fingers 450.

Follower 475 includes a pair of diametrically opposed retraction blocks 486 that project radially inwardly from an interior surface of the body 478 so as to fit within shuttle aperture 434, and which blocks serve as latching elements. A circumferential flange 488 with a chamfered proximal edge, and with alignment features 489 provided on its distal face are formed near the proximal end of body 478. Flange 488 snaps past housing ridges 310 during apparatus assembly. Four slots 492 in the proximal edge of body 478 define four damping fins 493 of the body.

A locking member for follower 475 to limit its rotation relative to the shuttle 375 is integrally formed with that follower in the apparatus of FIG. 22. Two such locking members, generally designated 496, are provided on diametrically opposite portions of the follower. Each locking member 496 is formed by an opening 500 that defines a finger or arm 502 that is resilient due to the follower construction. The radial inward face of each arm 502 near its projecting tip includes a key 504. Key 504 projects within a shuttle slot 428 to rotatably fix together shuttle 375 and locking member 496 and thereby follower 475, but is shiftable radially outward from the shuttle and toward the housing interior surface during injection by the plunger tabs 346 as described further below for unlocking the follower for rotation.

Figure 31A:
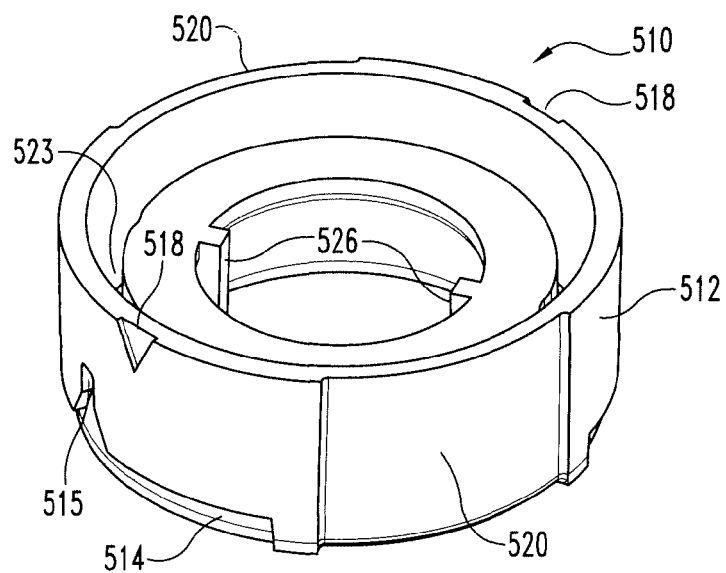
FIGS. 31A, 31B and 31C are respectively a top perspective, elevational, and longitudinal cross-sectional views of the damping collar of the apparatus of FIG. 22 shown separate from the other apparatus components.
Figure 31B:
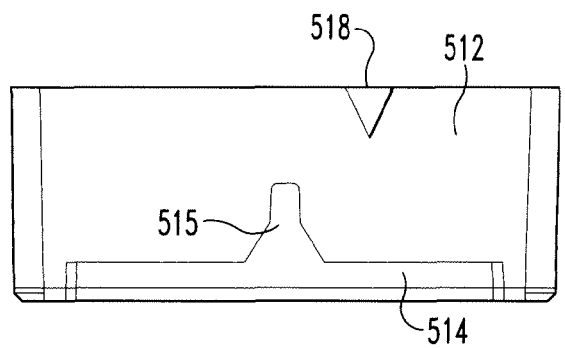
Figure 31C:
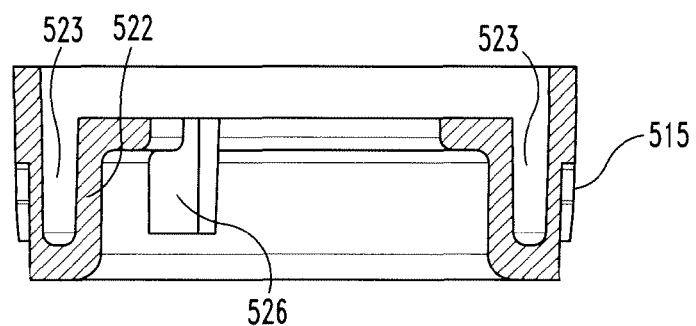

As further shown in FIGS. 31A-C, the grease or damping collar, generally designated 510, is molded from ABS plastic and includes a body 512 that has a cylindrical outer periphery. A pair of notches 514 each with a keying slot 515 is provided on the bottom edge of body 512. Notches 514 and keying slots 515 seat on the housing ridges 308 and keys 309 during assembly to rotatably lock the damping collar 510 to the apparatus housing 304. A pair of alignment features 518 matches the corresponding alignment features 489 of follower 475, which features facilitate assembly. A pair of notches 520 formed in the periphery of body 512 allow passage of housing ridges 310 during insertion of the collar 510 into the housing 304 during assembly. Body 512 includes a generally U-shaped wall portion 522 that defines an annular hollow or channel 523. A pair of ribs 526 protruding radially inward from wall portion 522 fit within shuttle keyways 442 such that shuttle 375 is rotatably fixed relative to the housing 304 via the collar 510.

A damping compound 530, such as fluorocarbon gel 836A available from Nye Lubricants, fills annular hollow 523. Follower fins 493 fit within hollow 523 such that compound 530 is disposed both radially inward and outward of such fins 493, resulting in a damping or delay effect as the follower fins 493 try to rotate relative to the U-shaped interior surface of wall portion 522 during operation.

Figure 32A:
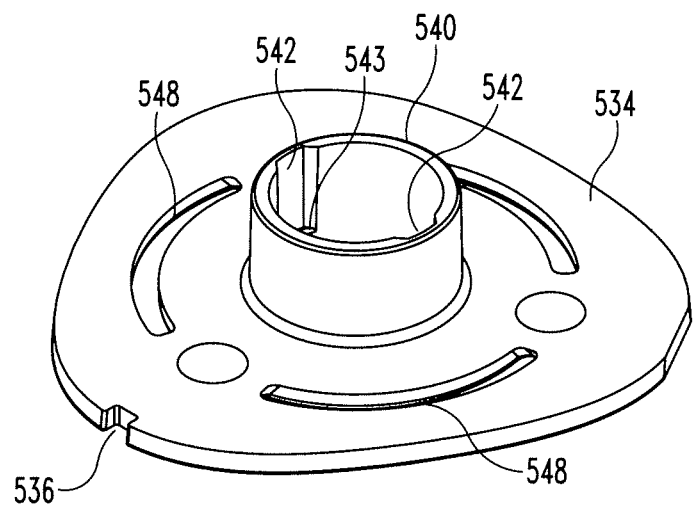
FIGS. 32A and 32B are respectively a top perspective and proximal end view of the housing base plate of the apparatus of FIG. 22 shown separate from the other apparatus components.
Figure 32B:
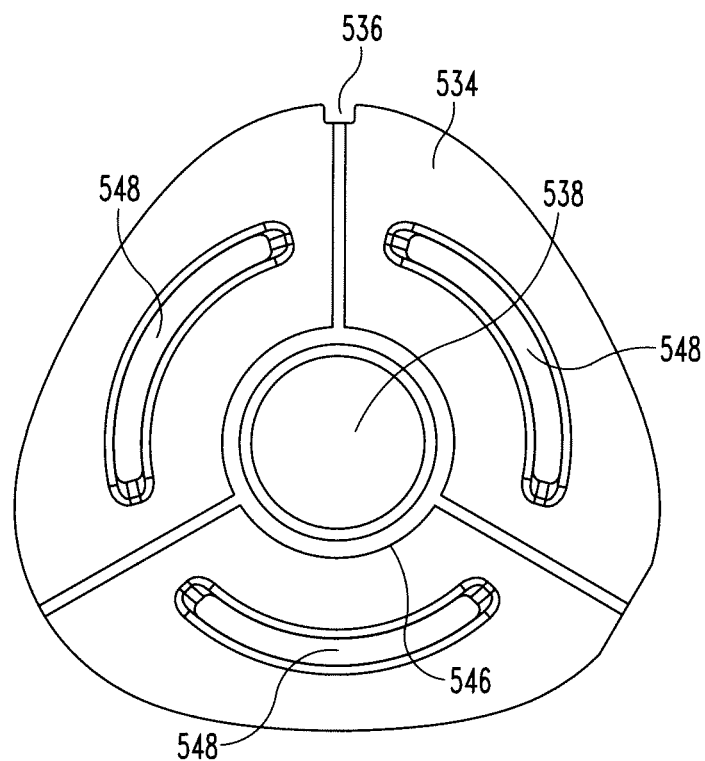

The injection site skin-contacting surface of the apparatus housing is formed of a base plate 534 made of a transparent ABS plastic and further shown in FIGS. 32A and 32B. Base plate 534 is generally trilobular and keyed at 536 to fit within the complementarily shaped proximal end of housing 304 where it is fixedly secured during manufacture, such as via UV-cured adhesives, ultrasonic welding or snap-fit. The central aperture 538 of plate 534 through which needle 322 moves during insertion is ringed by a distally extending collar 540. A pair of notches 542 formed in the interior surface of collar 540 form latching ledges 543. A colored targeting guide 546 to help a user visualize where needle 322 is to enter the skin is pad printed on the proximal surface of plate 534. A set of three arcuate slots 548 are formed through plate 534.

Figure 33A:
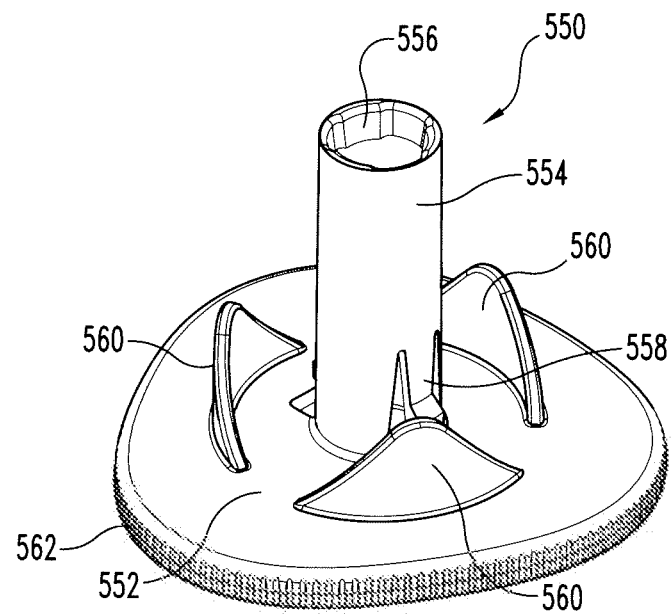
FIGS. 33A and 33B are respectively a top perspective view and a longitudinal cross sectional view of the overcap of the apparatus of FIG. 22 shown separate from the other apparatus components.
Figure 33B:
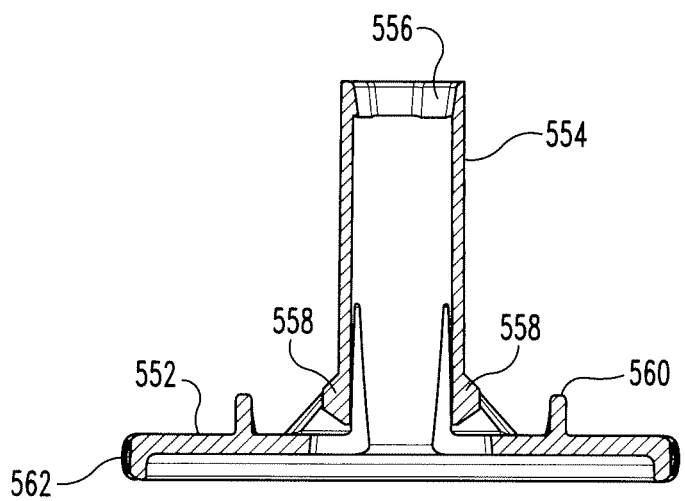

An overcap 550 made of a translucent ABS plastic and further shown in FIGS. 33A and 33B includes a base 552 and an upstanding collar member 554. Needle shield 526 inserts within collar member 554 during assembly such that a series of inwardly extending protrusions 556 of member 554 engage the distal edge of needle shield rib 326. A pair resilient tangs 558 formed into collar member 554 releasably engages latching ledges 543 to connect overcap 550 to housing base plate 534. A series or three arcuate cams 560 concentric with member 554 project distally from the distal face of base 552 in registry with slots 548 of plate 534. The periphery 562 of base 552 is knurled with straight ridges for ease of gripping by a user.

Figure 34A:
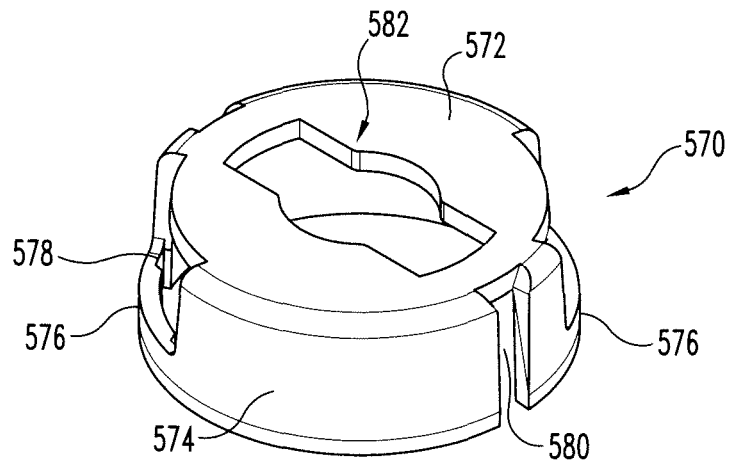
FIGS. 34A, 34B and 34C are respectively a top perspective, distal end, and elevational views of the trigger lock cup of the apparatus of FIG. 22 shown separate from the other apparatus components.
Figure 34B:
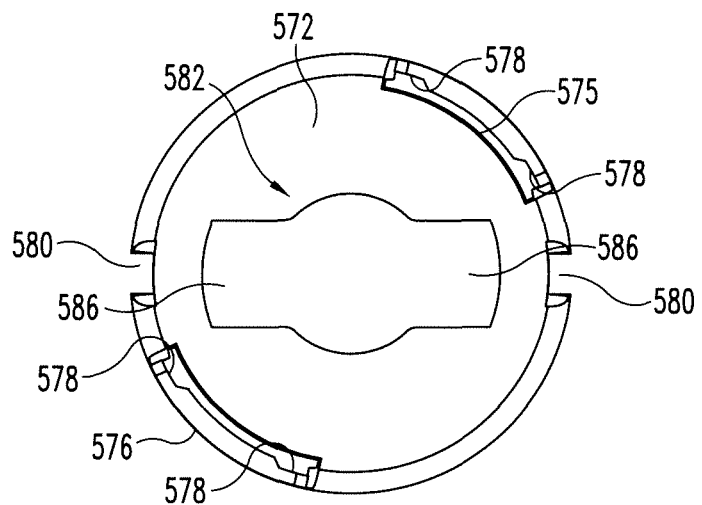
Figure 34C:
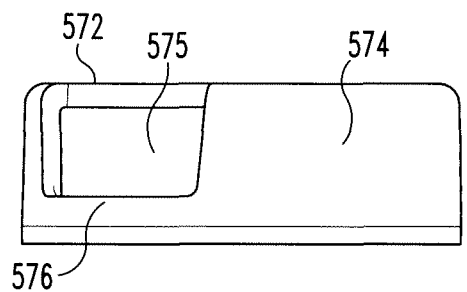

The locking and triggering of apparatus 300 involves an activation assembly disposed at the distal end of apparatus 300. This assembly includes a trigger lock cup 570, a trigger locking sleeve 590, and an activation button 620. The lock cup 570 is made of ABS plastic and is further shown in FIGS. 34A-C. Lock cup 570 includes a disc-shaped upper flange 572 with a depending lip 574. A pair of diametrically opposed apertures 575 provided in lip 572 form a pair of flexure arms 576. A pair of detents 578 is formed in the radial inward surface of each flexure arm 576 adjacent the opposite angular ends of each aperture 575. A pair of opposed slots 580 is formed along the entire height of lip 572. Lock cup 570 is assembled onto shuttle upper piece 380 during apparatus manufacture such that flexure arms 576 snap fit over retention tab portions 402, which snap fit assembly permits selective relative rotational motion between positions at which detent nub portions 404 fit detents 578. This detent connection aids in keeping the lock cup 570 in one of two preferred angular or rotational positions relative to the shuttle 375 and housing 304, but which detent connection can be overcome when the locking cup is to be moved between such positions by rotation of the locking sleeve 590.

Lock cup 570 includes a lock slot 582 formed through upper flange 572. Lock slot 582 includes a circular central region 584 with oppositely radially extending enlarged regions 586. When lock cup 570 is in a first preferred angular position relative to the shuttle, the enlarged regions 586 are partially offset from windows 392, which results in upper flange 572 being in close radial proximity to plunger distal ends 341 extending through the windows 392, thereby preventing the splaying outward of such distal ends 341 necessary for release of hooks 342 from engagement with the shuttle. When lock cup 570 is in the second preferred angular position, enlarged slot regions 586 align with windows 392 such that flange 572 no longer backs up the distal ends 341 to prevent their splaying outward, thereby unlocking or no longer preventing the release of the distal ends 341 from engagement with the shuttle.

The trigger locking sleeve 590 is made of ABS plastic and is further shown in FIGS. 35A-D. Locking sleeve 590 includes a main body portion 592 that is knurled with straight ridges for ease of gripping. A pad printed indicator mark 594 provided on body portion 592 is in axial alignment with housing alignment marking 316 when the locking sleeve 590 is not locking or preventing the plunging of activation button 620. When indicator mark 594 is angularly spaced from alignment marking 316 as shown in FIG. 22, the locking sleeve 590 prevents plunging of button 620. Locking sleeve 590 includes a stepped down portion 596 at its proximal end region that fits within the upper portion of housing 304. A circumferential groove 597 in the outer cylindrical periphery of sleeve portion 596 receives housing ring 312 to allow rotational motion but to prevent axial motion therebetween. Diametrically opposed notches 599 in the proximal edge of sleeve portion 596 accommodate the distal ends of housing ridges 314 to limit the extent of locking sleeve rotation. A further orientation notching 600 in one of the notches 599 can be used to align with alignment marking 316 during assembly.

Figure 35A:
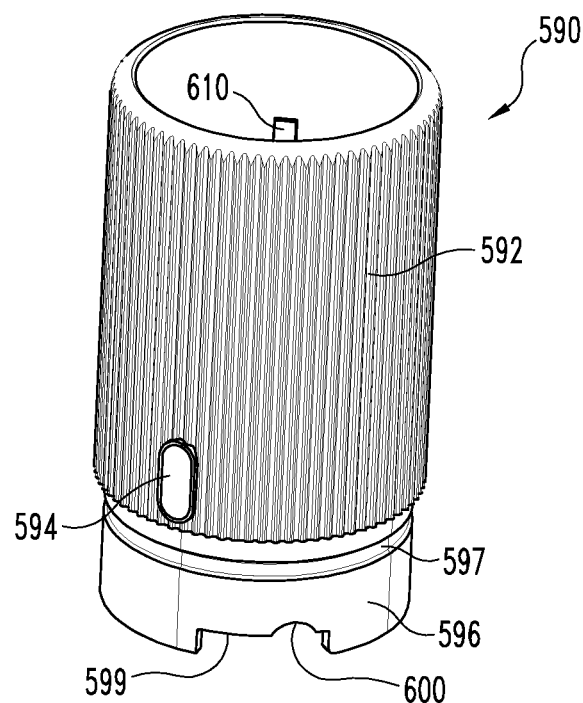
FIGS. 35A, 35B, 35C and 35D are respectively a top perspective, rear elevational, distal end and longitudinal cross-sectional views of the trigger locking sleeve of the apparatus of FIG. 22 shown separate from the other apparatus components.
Figure 35B:
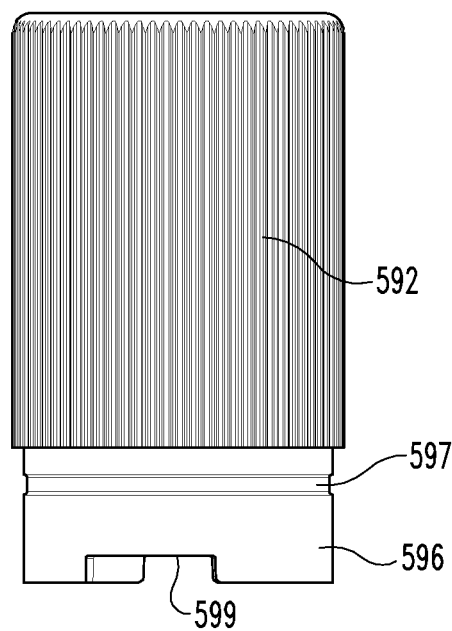
Figure 35C:
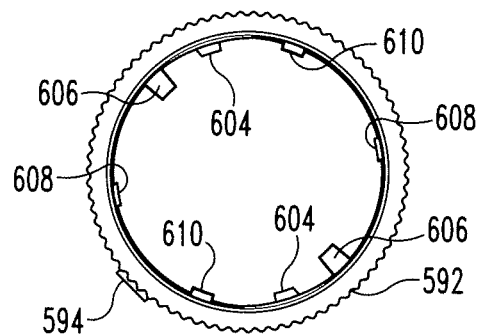
Figure 35D:
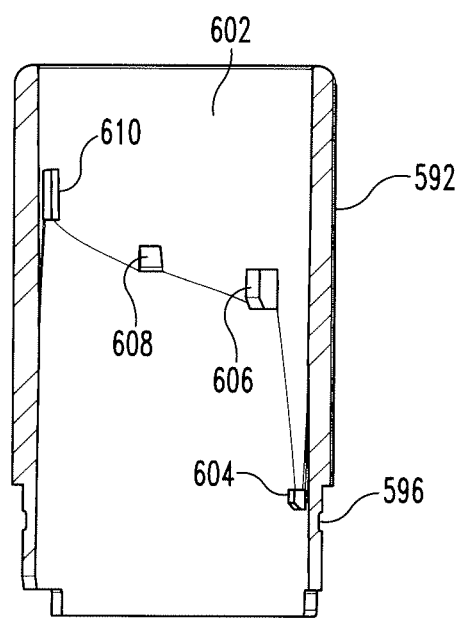
Figure 36A:
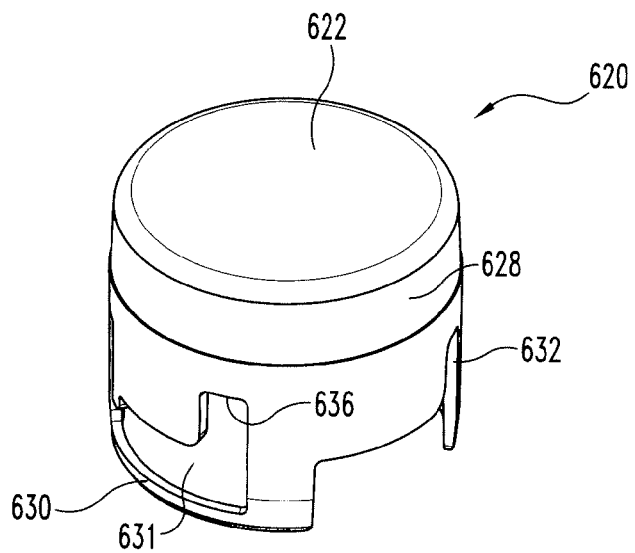
FIGS. 36A, 36B, 36C and 36D are respectively a top perspective, first and second elevational, and longitudinal cross-sectional views of the activation button of the apparatus of FIG. 22 shown separate from the other apparatus components.
Figure 36B:
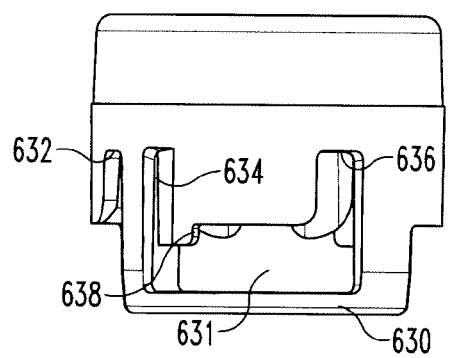
Figure 36C:
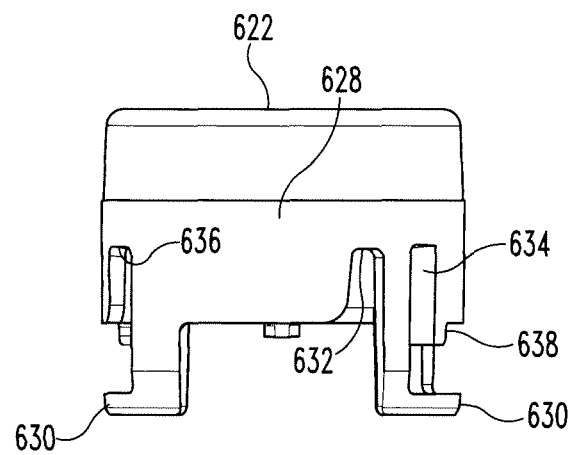
Figure 36D:
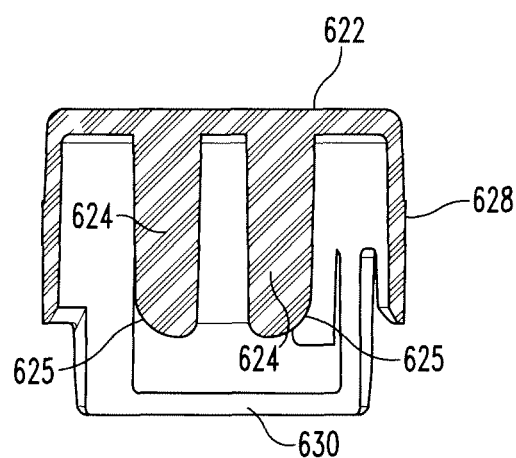

As best shown in FIG. 35D, the interior surface 602 of locking sleeve 605 that defines its hollow interior includes a series of pairs of diametrically projections including locking sleeve lock nubs 604, trigger lock rotation nubs 606, button lock tabs 608 and button travel nubs 610. The opposed lock nubs 604 are positioned at a first axial location for operational engagement with lock ribs 424 on the shuttle as described below. The opposed trigger lock rotation nubs 606 are disposed distally of nubs 604 in an angularly spaced relationship therewith, and fit within lock cup slots 580 so as to rotatably lock together lock cup 570 with trigger locking sleeve 590. The opposed button lock tabs 608 are disposed distally of nubs 606 and are in angularly spaced relationship with both lock nubs 604 and rotation nubs 606. The opposed button travel nubs 610 are disposed distally of lock tabs 608 and are in angularly spaced relationship with all of lock nubs 604, rotation nubs 606 and lock tabs 608.

The activation button 620 is made of ABS plastic and is further shown in FIGS. 36A-D. Button 620 includes an end disc 622 with a skirt 628 extending proximally from its outer periphery. End disc 622 has a distal face upon which a force can be directly applied by a user to selectively plunge the button. Depending from the underside of disc 622 is a pair of diametrically aligned activation legs 624. Button 620 is rotatably fixed to plunger element 330 by each leg 624 fitting between a pair of flanges 347 formed as part of each plunger prong distal end 341. Due to this rotatable fixation, in conjunction with the rotatable fixing of the plunger element to the shuttle, the rotatable fixing of the shuttle to the damping collar, and the rotatable fixing of the damping collar to the housing, the button 620 does not rotate relative to the housing 304. The proximal ends 625 of legs 624 are shaped to directly engage and force outward the angled ledges 348 of plunger arms 340 during button plunging.

Button skirt 628 is provided with a pair of depending flexure arms 630 that form apertures 631. Notches 632 and 634 in the proximal edge of skirt 628 adjacent an axially extending portion of each arm 630 promote flexure of the arm. The edge of skirt 628 above the angularly extending portion of each flexure arm 630 includes a upwardly projecting activation travel slot 636 as well as a downwardly extending rotation stop 638. Button 620 is assembled onto locking sleeve 590 during apparatus manufacture such that flexure arms 630 snap fit over button travel nubs 610 that insert into apertures 631, and with legs 624 fitting between flanges 347. This snap fit assembly prevents button distal withdrawal while permitting the locking sleeve 590 to be rotated a select distance relative to the button. The locking sleeve can rotate between an arrangement where travel nubs 610 abut stops 638, in which arrangement the sleeve is disposed in FIG. 22, and an arrangement where travel nubs 610 reach the end of the aperture 631 and are aligned axially with slots 636, in which arrangement the button is able to be plunged within the locking sleeve. When button 620 is so plunged by a user, flexure arms 630 snap fit over button lock tabs 608 that insert into apertures 63Ito hold button 620 in a plunged position after the user removes the force, which is a visual indication to the user that the apparatus has been used.

The construction of the inventive delay mechanism shown in apparatus 300 will be further understood in view of a description of its operation. With the apparatus initially configured as in FIGS. 22 and 23, the user must first remove the overcap 550. Prior to overcap removal, any user attempt to rotate the locking sleeve 590 to an unlocked state at which alignment features 594 and 316 are axially aligned is prevented by the direct abutment of trigger locking sleeve lock nubs 604 with shuttle lock ribs 424 positioned angularly adjacent thereto. In addition, any user attempt to plunge button 620 is prevented by the locking sleeve 590 due to the abutting of the edge of skirt 628 with button travel nubs 610.

The overcap 550 is manually removed by pulling it proximally off of the housing. The initial extent of such removal can be made easier by twisting the overcap relative to the housing, which twisting, due to the camming effect of cams 560 against plate 534, shifts the overcap proximally. This overcap removal pulls the needle shield 324 off of needle 322 and out of the housing due to the engagement of shield rib 326 by overcap protrusions 556. During this needle shield removal, the frictional engagement of the needle shield with the syringe results in the syringe and syringe carrier 354 moving proximally within shuttle 375 until plunger clips 366 abut ledge 333 to halt further proximal motion of the syringe relative to the plunger element 330 and shuttle 375. During this syringe carrier proximal movement, syringe carrier protruding portions 362 move proximally of shift arms fingers 450, such that the proximal ends of fingers 450 are forced radially inward into hollows 364 due to the camming of shuttle protrusions 452 by follower jam ledges 484 as the spring 455 urges the shuttle and follower axially apart. This camming movement unlatches protrusions 452 from ledges 484, allowing the shuttle 375, due to the biasing force provided by spring 455, to move distally from the follower 475 and within the housing 305 a short axial distance, such as about two millimeters, at which point the shuttle 375 is latched again with the follower via the follower blocks 486 engaging the surfaces defining apertures 434.

At this latched axial position of the shuttle 375, locking sleeve lock nubs 604 are now angularly clear of the axially shifted shuttle lock ribs 424, whereby a user can rotate the locking sleeve to an unlocked arrangement. In particular, the user can grip and manually rotate locking sleeve 590 relative to the housing 304 until the alignment features 594 and 316 are in registry, at which point the button travel nubs 610 have reached the end of the apertures 631 and are aligned axially with slots 636. During this locking sleeve rotation, the trigger lock cup 570 is simultaneously rotated due to the fitting of rotation nubs 606 within slots 580 to its second preferred angular position at which flange 572 no longer prevents the plunger ends from splaying outward. At this point, apparatus 30 is prepared for an injection.

When activation button 620 is subsequently pressed proximally by the user after the apparatus 300 is properly positioned on an injection site so as to trigger the injection, the proximal ends 625 of button legs 624 force plunger arms 340 to splay out such that activation hooks 342 unlatch from ledge 394 and the distal plunger ends 341 freely pass through windows 392 as plunger element 330 is automatically driven proximally by drive spring 350. Button 620 is retained in this plunged position within locking sleeve 590 by the engagement of flexure arms 630 with button lock tabs 608.

The proximal motion of plunger element 330 first results in syringe motion until syringe carrier 354 bottoms out within the shuttle 375, the overmolding 372 and the spring 455 dampening this bottoming out, at which time the tip of the injection needle 322 protrudes beyond the housing proximal end and into the injection site. Continued plunger motion slides piston 328 within barrel 320 to force the syringe contents through the needle. When plunger travel results in tabs 346 reaching locking member keys 504, the tabs 346 shift keys 504 radially outward from shuttle slot 428 so as to unlock the follower 475 for rotation.

Upon this unlocking, the urging by spring 455 of driver 460 proximally causes follower 475 to rotate within the housing and around the shuttle 375, with the damping compound 530 between the follower and damping collar 510 resisting this rotation. Rotation of the follower about the shuttle is driven by the continued axial motion of driver 460 until blocks 486 have shifted within shuttle aperture 434 into alignment with release slots 436. At this alignment, the shuttle 375 and follower 475 are effectively unlatched, allowing the shuttle 375, under the force of spring 455, to automatically and quickly shift distally and carry the needled syringe distally so as to retract the injection needle 322 within the housing 24. Shuttle 50 retracts until the diametrically opposed notches 416 fit around and abut the trigger lock rotation nubs 606, at which point the upper extent of the shuttle nests within the interior volume of activation button 620. Although shuttle 375 is no longer rotatably fixed by the damping collar 510 due to having been axially retracted therefore, shuttle 375 is still rotatably fixed relative to housing 304 due to the engagement of driver ribs 466 with shuttle channels 432 and driver keyways 473 with housing ridges 314. And, due to the engagement of rotation nubs 606 with notches 416, trigger locking sleeve 590 is rotatably locked with the housing, thereby indicating to the user that the apparatus 300 has been used. The apparatus can then be disposed of or otherwise handled by the user in the normal course.

While this invention has been shown and described as having preferred designs, the present invention may be modified within the spirit and scope of this disclosure. For example, while the delay mechanisms described above utilize rotating followers, a follower which moves in an axial direction to unlatch the shuttle may be provided within the scope of the invention. In particular, and as an example, a follower that is rotatably fixed and axially movable within the housing may be acted upon directly by a spring and without an additional intervening driver. The follower initially is axially retained by a locking member that, for example, is engaged with the housing body but which, upon passage of the plunger during injection, is disengaged so as to allow the follower to be shifted axially by the spring. A damping compound is provided between, for example, the outer radial periphery of the follower and the interior of the housing body. When the follow is so shifted axially, it unlatches the shuttle from the housing, such as by disengaging fingers of the shuttle that engage the housing, thereby allowing the shuttle to be retracted by an internal spring so as to thereby retract the carried syringe. This application is therefore intended to cover any variations, uses or adaptations of the invention using its general principles. Further, this application is intended to cover such departures from the present disclosure as come within known or customary practice in the art to which this invention pertains.

We claim:

1. In an automatic injection apparatus having a housing, a needled syringe with a plunger, and a plurality of biasing elements for moving the needled syringe in a first direction within the housing to extend the needle of the syringe beyond the housing, to advance the plunger to force syringe contents through the needle for an injection, and to retract the needle within the housing after injection, a delay mechanism comprising:
   a shuttle for the syringe, said shuttle including a first latching element;
   a follower including a second latching element and a cammable surface, said second latching element for cooperating with said first latching element to limit motion of said shuttle relative to said follower in a second direction opposite the first direction;
   a locking member movable within said housing from a locking position to a release position by engagement with the syringe plunger during an injection, said locking member, when in said locking position, preventing rotation of said follower relative to said shuttle, said locking member, when in said release position, allowing rotation of said follower relative to said shuttle;
   a damping compound between said follower and a supporting surface to dampen rotation of said follower relative to said shuffle;
   a driver rotatably fixed relative to said shuttle and including a camming surface; and
   a driver biasing element for forcing said driver from a first position to a second position when said locking member moves to said release position, whereby during movement of said driver to said second position, said driver camming surface engages said follower cammable surface to force said follower to rotate relative to said shuttle from a latching position, at which said first and second latching elements cooperate, to an unlatching position, at which said second latching element is disengaged from said first latching element to allow movement of said shuttle for retracting the syringe needle into the housing after injection.

2. The delay mechanism of claim 1 wherein said second latching element comprises a projecting tab, and wherein said first latching element comprises a portion of a tab track formed in said shuttle.

3. The delay mechanism of claim 2 wherein said tab track comprises an L-shaped slot, wherein said tab track portion forming said first latching element comprises a slot portion oriented transverse to the first direction.

4. The delay mechanism of claim 1 wherein said driver biasing element is operatively disposed between said driver and said shuttle, whereby said driver biasing element provides the biasing force on the shuttle for carrying the syringe to retract the needle into the housing after injection.

5. The delay mechanism of claim 1 wherein said driver and said follower comprise tubular bodies that are each concentrically arranged around said shuttle.

6. The delay mechanism of claim 1 wherein said supporting surface comprises a radially inner surface of a collar rotatably fixed relative to the apparatus housing.

7. The delay mechanism of claim 1 wherein said shuttle and said driver are each keyed to the apparatus housing to be axially shiftable and rotatably fixed relative to the housing.

8. The delay mechanism of claim 1 wherein said locking member comprises at least one key that fits within at least one slot in said shuttle to rotatably secure together said locking member and said shuttle, and wherein said at least one key fits within at least one notch of said follower when in said locking position to rotatably secure together said locking member and said follower.

9. The delay mechanism of claim 8 wherein said follower and said at least one key comprises a detented releasable connection to discourage premature motion of the locking member.

10. The delay mechanism of claim 1 wherein said camming surface and said cammable surface comprises directly engaging faces of ramp shaped projections.

11. The delay mechanism of claim 1 wherein said shuttle comprises a support against which acts the biasing element that moves the needled syringe in the first direction and advances the plunger.

12. The delay mechanism of claim 1 wherein said locking member comprises at least one flexure integrally formed with said follower and radially movable within said housing from a locking position to a release position by engagement with the syringe plunger during an injection.

13. The delay mechanism of claim 1 further comprising means for allowing said shuttle to shift axially relative to said follower front a first latched position to a second latched position during removal of a cap from the apparatus, wherein at said first latched position said shuttle cooperates with a trigger locking assembly to prevent apparatus triggering, and wherein at said second latched position said shuttle permits movement of the trigger locking assembly which allows for apparatus triggering.

14. The delay mechanism of claim 13 wherein said means for allowing said shuttle to shift axially relative to said follower from a first latched position to a second latched position comprises a plurality of shuttle shift arms including radial protrusions that latch with jam ledges provided on said follower when said plurality of shuttle shift arms are radially backed by a syringe carrier.

15. In an automatic injection apparatus, a delay mechanism comprising:
   a shuttle for a needled syringe of the apparatus;
   a movable member;
   means for limiting motion of said shuttle in a needle retraction direction;
   means for damping rotational motion of said movable member relative to said shuttle; and
   means for rotating said movable member relative to said shuttle from a first position to a second position to allow movement of said shuttle for retracting the needle of the syringe within the apparatus after injection.

16. The delay mechanism of claim 15 wherein said means for rotating said movable member comprises at least one resilient finger extending from a plunger of the needled syringe, and a straightening element on said shuttle for straightening and then releasing said at least one resilient finger to drive movable member rotation.

17. The delay mechanism of claim 15 wherein said means for rotating said movable member comprises a cammable surface on said movable member, a driver rotatably fixed relative to said shuttle and including a camming surface, and a biasing element for forcing said driver to move axially and rotate said movable member due to the direct driving engagement of said cammable surface by said camming surface.

18. The delay mechanism of claim 15 wherein said shuttle supportably holds a biasing element that advances the needled syringe for injection, whereby biasing of the shuttle for retracting the needle is not resisted by the biasing element that advances the needled syringe.

* * * * *

UNITED STATES PATENT AND TRADEMARK OFFICE
CERTIFICATE OF CORRECTION

| | | |
|---|---|---|
| PATENT NO. | : 8,409,138 B2 | Page 1 of 1 |
| APPLICATION NO. | : 12/529788 | |
| DATED | : April 2, 2013 | |
| INVENTOR(S) | : Adrian Benton James et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

In the Claims:

Column 19, Line 61 (In Line 25 of Claim 1) delete "shuffle;" and insert -- shuttle; -- therefor.

Column 20, Line 57 (In Line 3 of Claim 13) delete "front" and insert -- from -- therefor.

Signed and Sealed this
Twenty-seventh Day of August, 2013

Teresa Stanek Rea
*Acting Director of the United States Patent and Trademark Office*